US011504505B2

(12) United States Patent
Harding et al.

(10) Patent No.: US 11,504,505 B2
(45) Date of Patent: Nov. 22, 2022

(54) NEEDLE CAPTURE SAFETY INTERLOCK FOR CATHETER

(71) Applicant: Becton, Dickinson and Company, Franklin Lakes, NJ (US)

(72) Inventors: Weston Harding, Lehi, UT (US); John Stokes, Pleasant View, UT (US); Aaron Wang, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 202 days.

(21) Appl. No.: 16/736,532

(22) Filed: Jan. 7, 2020

(65) Prior Publication Data

US 2020/0139087 A1    May 7, 2020

Related U.S. Application Data

(63) Continuation of application No. 15/304,332, filed as application No. PCT/US2015/026536 on Apr. 17, 2015, now Pat. No. 10,625,054.

(Continued)

(51) Int. Cl.
*A61M 25/06* (2006.01)
*A61M 25/00* (2006.01)
(Continued)

(52) U.S. Cl.
CPC ........ *A61M 25/0618* (2013.01); *A61M 5/158* (2013.01); *A61M 5/3202* (2013.01);
(Continued)

(58) Field of Classification Search
CPC .......... A61M 25/0618; A61M 25/0097; A61M 25/0606; A61M 25/0631; A61M 5/158;
(Continued)

(56) References Cited

U.S. PATENT DOCUMENTS 3,585,996 A    6/1971 Reynolds et al.
4,332,249 A    6/1982 Joslin
(Continued)

FOREIGN PATENT DOCUMENTS

AU    2006203663 B2    8/2006
AU    2006203664 A1    2/2008
(Continued)

OTHER PUBLICATIONS

Singapore Office Action dated Jan. 29, 2020 in Singapore Patent Application No. 11201708370P.
(Continued)

*Primary Examiner* — Tasnim Mehjabin Ahmed
(74) *Attorney, Agent, or Firm* — Dickinson Wright PLLC

(57) ABSTRACT

A catheter assembly includes a flexible catheter (22), a needle (12) having a sharp distal tip, the needle (12) disposed in the flexible catheter (22) and moving from a first position that exposes the needle (12) to a second position, an outer member (26) that is configured to engage and disengage a catheter hub (14), an inner member (28) disposed in the outer member (26), and a needle protection (30) member disposed in the inner member (28), the needle protection member (30) enclosing at least a portion of the needle (12) when the needle (12) is in the second position.

19 Claims, 44 Drawing Sheets

Related U.S. Application Data

(60) Provisional application No. 62/077,760, filed on Nov. 10, 2014, provisional application No. 61/981,312, filed on Apr. 18, 2014, provisional application No. 61/981,223, filed on Apr. 18, 2014.

(51) Int. Cl.
*A61M 5/32* (2006.01)
*A61M 5/158* (2006.01)
*A61M 39/24* (2006.01)
*A61M 5/34* (2006.01)
*A61M 39/06* (2006.01)
*A61M 39/22* (2006.01)

(52) U.S. Cl.
CPC ........ *A61M 5/3213* (2013.01); *A61M 5/3232* (2013.01); *A61M 5/34* (2013.01); *A61M 25/0097* (2013.01); *A61M 25/0606* (2013.01); *A61M 25/0631* (2013.01); *A61M 39/24* (2013.01); *A61M 5/3273* (2013.01); *A61M 2039/064* (2013.01); *A61M 2039/066* (2013.01); *A61M 2039/0673* (2013.01); *A61M 2039/226* (2013.01)

(58) Field of Classification Search
CPC .............. A61M 5/3202; A61M 5/3213; A61M 5/3232; A61M 5/34; A61M 5/3273; A61M 39/24
See application file for complete search history.

(56) References Cited

U.S. PATENT DOCUMENTS

| | | | |
|---|---|---|---|
| 4,387,879 A | 6/1983 | Tauschinski | |
| 4,524,805 A | 6/1985 | Hoffman | |
| 4,622,964 A | 11/1986 | Flynn | |
| 4,762,516 A | 8/1988 | Luther et al. | |
| 4,809,679 A | 3/1989 | Shimonaka et al. | |
| 4,842,591 A | 6/1989 | Luther | |
| 4,850,961 A | 7/1989 | Wanderer | |
| 4,871,356 A | 10/1989 | Haindl et al. | |
| 4,917,668 A | 4/1990 | Haindl | |
| 4,946,133 A | 8/1990 | Johnson et al. | |
| 4,948,092 A | 8/1990 | Kasper et al. | |
| 4,978,344 A | 12/1990 | Dombrowski et al. | |
| 5,000,740 A | 3/1991 | Ducharme et al. | |
| 5,032,116 A | 7/1991 | Peterson et al. | |
| 5,053,014 A | 10/1991 | Van Heugten | |
| 5,092,845 A | 3/1992 | Chang | |
| 5,108,380 A | 4/1992 | Herlitze et al. | |
| 5,215,525 A | 6/1993 | Sturman | |
| 5,215,528 A | 6/1993 | Purdy et al. | |
| 5,228,453 A | 7/1993 | Sepetka | |
| 5,290,246 A | 3/1994 | Yamamoto et al. | |
| 5,300,045 A | 4/1994 | Plassche, Jr. | |
| 5,322,518 A | 6/1994 | Schneider et al. | |
| 5,328,482 A | 7/1994 | Sircom et al. | |
| 5,348,544 A | 9/1994 | Sweeney et al. | |
| 5,391,152 A | 2/1995 | Patterson | |
| 5,405,323 A | 4/1995 | Rogers | |
| 5,419,766 A | 5/1995 | Chang et al. | |
| 5,423,766 A | 6/1995 | Di Cesare | |
| 5,458,658 A | 10/1995 | Sircom | |
| 5,501,675 A | 3/1996 | Erskine | |
| 5,538,508 A | 7/1996 | Steyn | |
| 5,558,651 A | 9/1996 | Crawford et al. | |
| 5,575,777 A | 11/1996 | Cover et al. | |
| 5,584,809 A | 12/1996 | Gaba | |
| 5,596,996 A | 1/1997 | Johanson | |
| 5,662,610 A | 9/1997 | Sircom | |
| 5,697,907 A | 12/1997 | Gaba | |
| 5,718,688 A | 2/1998 | Wozencroft | |
| 5,749,857 A | 5/1998 | Cuppy | |
| 5,772,636 A | 6/1998 | Brimhall et al. | |
| 5,817,069 A | 10/1998 | Arnett | |
| 5,851,196 A | 12/1998 | Arnett | |
| 5,858,002 A | 1/1999 | Jesch | |
| 5,911,710 A | 6/1999 | Barry et al. | |
| 5,951,515 A | 9/1999 | Osterlind | |
| 5,954,698 A | 9/1999 | Pike | |
| 5,867,490 A | 10/1999 | Pike | |
| 6,001,080 A | 12/1999 | Kuracina et al. | |
| 6,042,876 A | 3/2000 | Deem | |
| 6,117,108 A | 9/2000 | Woehr et al. | |
| 6,213,978 B1 | 4/2001 | Voyten | |
| 6,221,047 B1 | 4/2001 | Greene et al. | |
| 6,224,569 B1 | 5/2001 | Brimhall et al. | |
| 6,379,333 B1 | 4/2002 | Brimhall et al. | |
| 6,425,884 B1 | 7/2002 | Wemmert et al. | |
| 6,506,181 B2 | 1/2003 | Meng et al. | |
| 6,595,981 B2 | 7/2003 | Huet | |
| 6,616,630 B1 | 9/2003 | Woehr | |
| 66,452,486 | 11/2003 | Biaiecki et al. | |
| 6,709,419 B2 | 3/2004 | Woehr | |
| 6,749,588 B1 | 6/2004 | Howell et al. | |
| 6,972,002 B2 | 12/2005 | Thome | |
| RE38,996 E | 2/2006 | Crawford et al. | |
| 7,226,434 B2 | 6/2007 | Carlyon et al. | |
| 7,530,965 B2 | 5/2009 | Villa et al. | |
| 7,597,681 B2 | 10/2009 | Sutton et al. | |
| 7,632,245 B1 | 12/2009 | Cowan et al. | |
| 7,651,476 B2 | 1/2010 | Kohler | |
| 7,682,340 B2 | 3/2010 | Funamura et al. | |
| 7,736,332 B2 | 6/2010 | Carlyon et al. | |
| 7,736,339 B2 | 6/2010 | Woehr et al. | |
| 7,988,664 B2 | 8/2011 | Fiser et al. | |
| 8,308,691 B2 | 11/2012 | Woehr et al. | |
| 8,328,762 B2 | 12/2012 | Woehr et al. | |
| 8,333,735 B2 | 12/2012 | Woehr et al. | |
| 8,337,463 B2 | 12/2012 | Woehr et al. | |
| 8,348,893 B2 | 1/2013 | Carlyon | |
| 8,357,119 B2 | 1/2013 | Stout et al. | |
| 8,361,020 B2 | 1/2013 | Stout | |
| 8,361,038 B2 | 1/2013 | McKinnon et al. | |
| 8,382,718 B2 | 2/2013 | Woehr | |
| 8,388,583 B2 | 3/2013 | Stout et al. | |
| 8,419,688 B2 | 4/2013 | Woehr et al. | |
| 8,460,247 B2 | 6/2013 | Woehr et al. | |
| 8,469,928 B2 | 6/2013 | Stout et al. | |
| 8,496,623 B2 | 7/2013 | Burkholz | |
| 8,523,828 B2 | 9/2013 | Callahan | |
| 8,540,728 B2 | 9/2013 | Woehr et al. | |
| 8,591,468 B2 | 11/2013 | Woehr et al. | |
| 8,597,249 B2 | 12/2013 | Woehr et al. | |
| 8,764,711 B2 | 7/2014 | Kuracina et al. | |
| 8,827,965 B2 | 9/2014 | Woehr et al. | |
| 8,926,564 B2 | 1/2015 | King et al. | |
| 8,939,938 B2 | 1/2015 | Funamura et al. | |
| 8,951,230 B2 | 2/2015 | Tanabe et al. | |
| 9,056,188 B2 | 6/2015 | Hager et al. | |
| 9,089,671 B2 | 7/2015 | Stout et al. | |
| 9,114,241 B2 | 8/2015 | Stout et al. | |
| 9,149,625 B2 | 10/2015 | Woehr et al. | |
| 9,149,626 B2 | 10/2015 | Woehr et al. | |
| 9,180,277 B2 | 11/2015 | Erskine | |
| 9,278,195 B2 | 3/2016 | Erskine | |
| 9,370,641 B2 | 6/2016 | Woehr et al. | |
| 9,408,632 B2 | 8/2016 | Erskine | |
| 9,592,152 B2 | 3/2017 | Griffis et al. | |
| 9,717,886 B2 | 8/2017 | Kuehn et al. | |
| 10,625,054 B2 * | 4/2020 | Harding | A61M 5/158 |
| 10,729,890 B2 | 8/2020 | Harding et al. | |
| 2001/0053895 A1 | 12/2001 | Vaillancourt | |
| 2002/0128604 A1 | 9/2002 | Nakajima | |
| 2002/0169418 A1 | 11/2002 | Menzi et al. | |
| 2003/0057392 A1 | 3/2003 | Ito | |
| 2003/0060774 A1 | 3/2003 | Woehr et al. | |
| 2003/0195471 A1 | 10/2003 | Woehr et al. | |
| 2004/0116856 A1 | 6/2004 | Woehr et al. | |
| 2004/0204689 A1 | 10/2004 | Lynn | |
| 2004/0225260 A1 | 11/2004 | Villa et al. | |
| 2005/0010176 A1 | 1/2005 | Dikeman et al. | |

(56) References Cited

U.S. PATENT DOCUMENTS

| | | |
|---|---|---|
| 2005/0043684 A1 | 2/2005 | Basta et al. |
| 2005/0075609 A1 | 4/2005 | Latona |
| 2005/0107740 A1 | 5/2005 | Jensen et al. |
| 2005/0113755 A1 | 5/2005 | Greene et al. |
| 2006/0074384 A1 | 4/2006 | Kohler |
| 2006/0155245 A1 | 7/2006 | Woehr |
| 2006/0178635 A1 | 8/2006 | Callaway |
| 2006/0200080 A1 | 9/2006 | Abulhaj |
| 2006/0264828 A1 | 11/2006 | Woehr et al. |
| 2007/0038186 A1* | 2/2007 | Sutton ............... A61M 25/0618 604/164.08 |
| 2007/0083162 A1 | 4/2007 | O'Reagan et al. |
| 2007/0129689 A1 | 6/2007 | Woehr et al. |
| 2007/0176414 A1 | 8/2007 | McBee et al. |
| 2007/0270754 A1 | 11/2007 | Soderholm et al. |
| 2008/0065015 A1 | 3/2008 | Fisher et al. |
| 2008/0097343 A1 | 4/2008 | Woehr |
| 2008/0140004 A1 | 6/2008 | Thorne et al. |
| 2008/0140011 A1 | 6/2008 | Hager et al. |
| 2008/0147009 A1 | 6/2008 | Nilsson et al. |
| 2008/0208132 A1 | 8/2008 | Funamura et al. |
| 2008/0243086 A1 | 10/2008 | Hager et al. |
| 2009/0137958 A1 | 5/2009 | Erskine |
| 2009/0163861 A1 | 6/2009 | Carlyon |
| 2009/0182280 A1 | 7/2009 | Glowacki et al. |
| 2009/0281499 A1 | 11/2009 | Harding |
| 2009/0312711 A1 | 12/2009 | Brimhall |
| 2010/0137803 A1 | 6/2010 | Funamura et al. |
| 2010/0191189 A1 | 7/2010 | Harding et al. |
| 2010/0204648 A1 | 8/2010 | Stout et al. |
| 2010/0204660 A1 | 8/2010 | McKinnon et al. |
| 2010/0217208 A1 | 8/2010 | Snow |
| 2010/0222746 A1 | 9/2010 | Burkholz |
| 2011/0054403 A1 | 3/2011 | Tanabe et al. |
| 2011/0060286 A1 | 3/2011 | Tanabe et al. |
| 2011/0160662 A1 | 6/2011 | Stout et al. |
| 2011/0213307 A1 | 9/2011 | Kawai et al. |
| 2011/0288482 A1 | 11/2011 | Farrell et al. |
| 2011/0301551 A1 | 12/2011 | Koehler et al. |
| 2012/0065612 A1 | 3/2012 | Stout et al. |
| 2012/0078200 A1 | 3/2012 | Woehr et al. |
| 2012/0123354 A1 | 5/2012 | Woehr |
| 2012/0136311 A1 | 5/2012 | Knutsson et al. |
| 2012/0220957 A1 | 8/2012 | Kuracina et al. |
| 2012/0238966 A1 | 9/2012 | Kuracina et al. |
| 2012/0277679 A1 | 11/2012 | Steube |
| 2013/0030370 A1 | 1/2013 | Walker et al. |
| 2013/0090607 A1 | 4/2013 | McKinnon et al. |
| 2013/0090609 A1 | 4/2013 | Sonderegger et al. |
| 2013/0178807 A1 | 7/2013 | Baid |
| 2013/0184645 A1 | 7/2013 | Baid |
| 2013/0226141 A1 | 8/2013 | King et al. |
| 2013/0245587 A1 | 9/2013 | Tremblay |
| 2013/0253443 A1 | 9/2013 | Woehr et al. |
| 2013/0324930 A1 | 12/2013 | Fuchs et al. |
| 2014/0012203 A1 | 1/2014 | Woehr et al. |
| 2014/0018738 A1 | 1/2014 | Steube |
| 2014/0058329 A1 | 2/2014 | Walker et al. |
| 2014/0276434 A1 | 9/2014 | Woehr et al. |
| 2014/0296829 A1 | 10/2014 | White et al. |
| 2014/0303561 A1 | 10/2014 | Li |
| 2014/0364809 A1 | 12/2014 | Isaacson et al. |
| 2015/0151088 A1 | 6/2015 | Lim et al. |
| 2015/0224267 A1 | 8/2015 | Farrell et al. |
| 2016/0015941 A1 | 1/2016 | Tanabe et al. |
| 2016/0106959 A1 | 4/2016 | Woehr |
| 2016/0158503 A1 | 6/2016 | Woehr |
| 2016/0158526 A1 | 6/2016 | Woehr |
| 2017/0348518 A1 | 12/2017 | Ma et al. |

FOREIGN PATENT DOCUMENTS

| | | |
|---|---|---|
| CA | 2133053 A1 | 3/1995 |
| CN | 1758929 A | 4/2006 |
| CN | 1871043 A | 11/2006 |
| CN | 101112639 A | 1/2008 |
| CN | 101573153 A | 11/2009 |
| CN | 101573154 A | 11/2009 |
| CN | 101791447 A | 8/2010 |
| CN | 202005932 U | 10/2011 |
| CN | 202682467 U | 1/2013 |
| CN | 106470607 A | 3/2017 |
| EP | 0352928 A1 | 1/1990 |
| EP | 1558311 A1 | 8/2008 |
| EP | 2228093 A1 | 9/2010 |
| EP | 2343095 A1 | 7/2011 |
| EP | 2489393 A1 | 8/2012 |
| EP | 2666543 A1 | 3/2013 |
| EP | 2803376 A1 | 11/2014 |
| JP | H1057497 A | 3/1998 |
| JP | 2001-514943 A | 9/2001 |
| JP | 2001514943 A | 9/2001 |
| JP | 2002126080 A | 5/2002 |
| JP | 2002263197 A | 9/2002 |
| JP | 2008173206 A | 7/2008 |
| JP | 2010099534 A | 5/2010 |
| JP | 2001115630 A | 6/2011 |
| JP | 3170612 U | 8/2011 |
| JP | 2012-517326 A | 8/2012 |
| JP | 2012517326 A | 8/2012 |
| JP | 2013115630 A | 6/2013 |
| JP | 2013192868 A | 9/2013 |
| JP | 2017533770 A | 11/2017 |
| SG | 173383 A1 | 8/2011 |
| WO | 1993005840 A2 | 4/1993 |
| WO | 1995022364 A1 | 8/1995 |
| WO | 9924092 | 5/1999 |
| WO | 2001012249 A1 | 2/2001 |
| WO | 0193940 A2 | 12/2001 |
| WO | 0195958 | 12/2001 |
| WO | 2903011381 A1 | 2/2003 |
| WO | 2004004819 A1 | 1/2004 |
| WO | 2005042073 A1 | 5/2005 |
| WO | 2008064332 A2 | 5/2008 |
| WO | 2009154824 A1 | 12/2009 |
| WO | 2013014639 A1 | 1/2013 |
| WO | 2013051242 A1 | 4/2013 |
| WO | 2013052666 A1 | 4/2013 |
| WO | 2013137348 A1 | 9/2013 |
| WO | 2013162461 A1 | 10/2013 |
| WO | 2014054166 A1 | 4/2014 |
| WO | 2014126865 A1 | 8/2014 |
| WO | 2014197656 A1 | 12/2014 |
| WO | 2015161296 A1 | 10/2015 |
| WO | 2016077234 A1 | 5/2016 |
| WO | 2014162377 A1 | 2/2017 |

OTHER PUBLICATIONS

Japanese Office Action dated Jan. 28, 2020 in Japanese Patent Application No. 2017-554341.
Singapore Office Action dated Nov. 12, 2019 in Singapore Patent Application No. 11201708371S.
Brazilian Office Action dated Feb. 4, 2020 in Brazilian Patent Application No. 112015030658-6.
US 5,755,409, 8/1979, Sigmund (withdrawn)
Medikit Co., Ltd., Dual Protection Safety I.V. Catheter—Supercath 5: A New Generation of Safety I.V. Catheter, Medikit, Manufacturer Togo Medikit Co., Ltd., IVBB080001-B61G2S, Approximately 2008 (3 Pages Total).
Jul. 21, 2015, Written Opinion issued for related application No. PCT/US2015/026536.
Jul. 21, 2015, International Search report issued for related application No. PCT/US2015/026536.

* cited by examiner

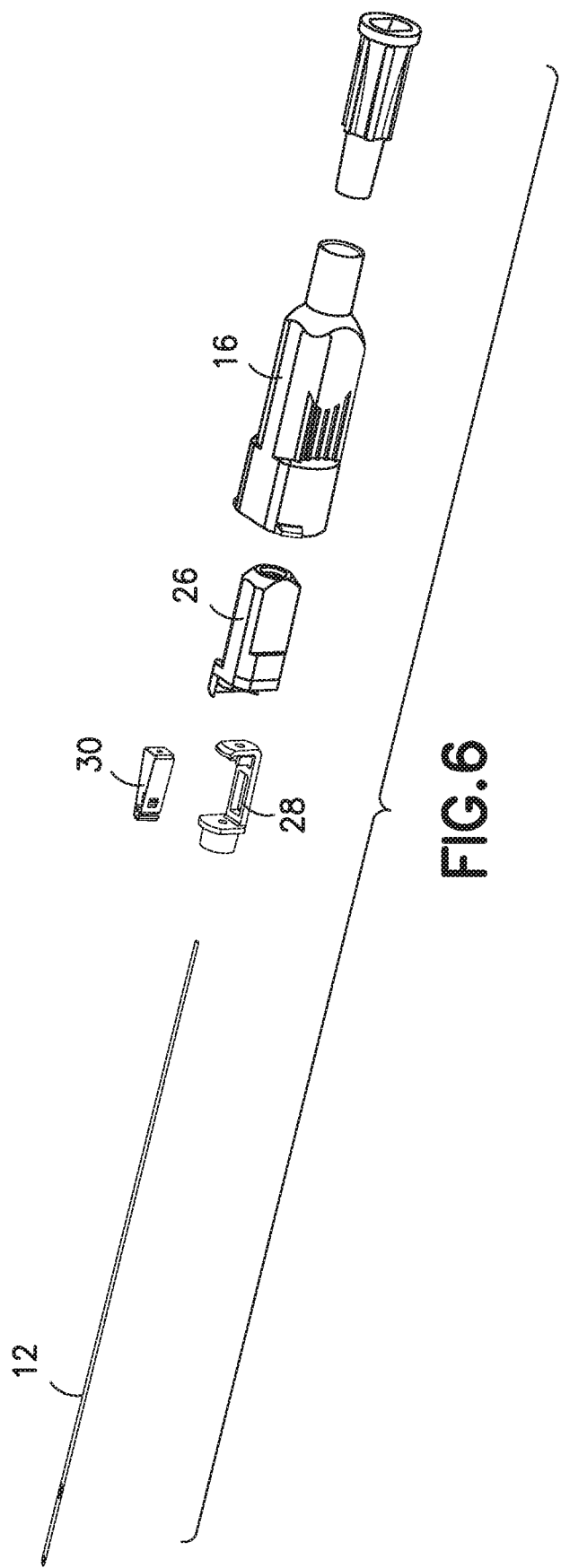

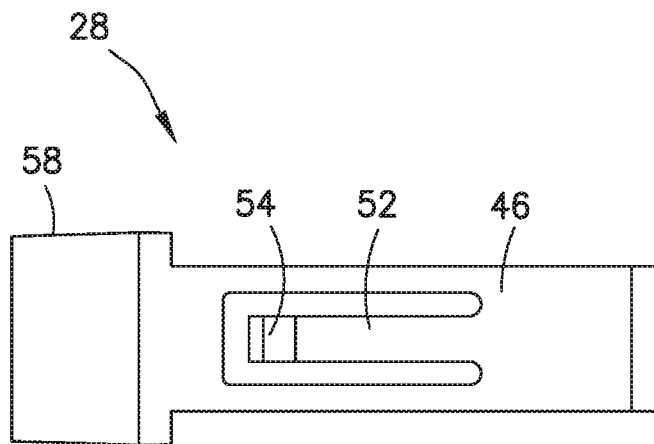
FIG.9G
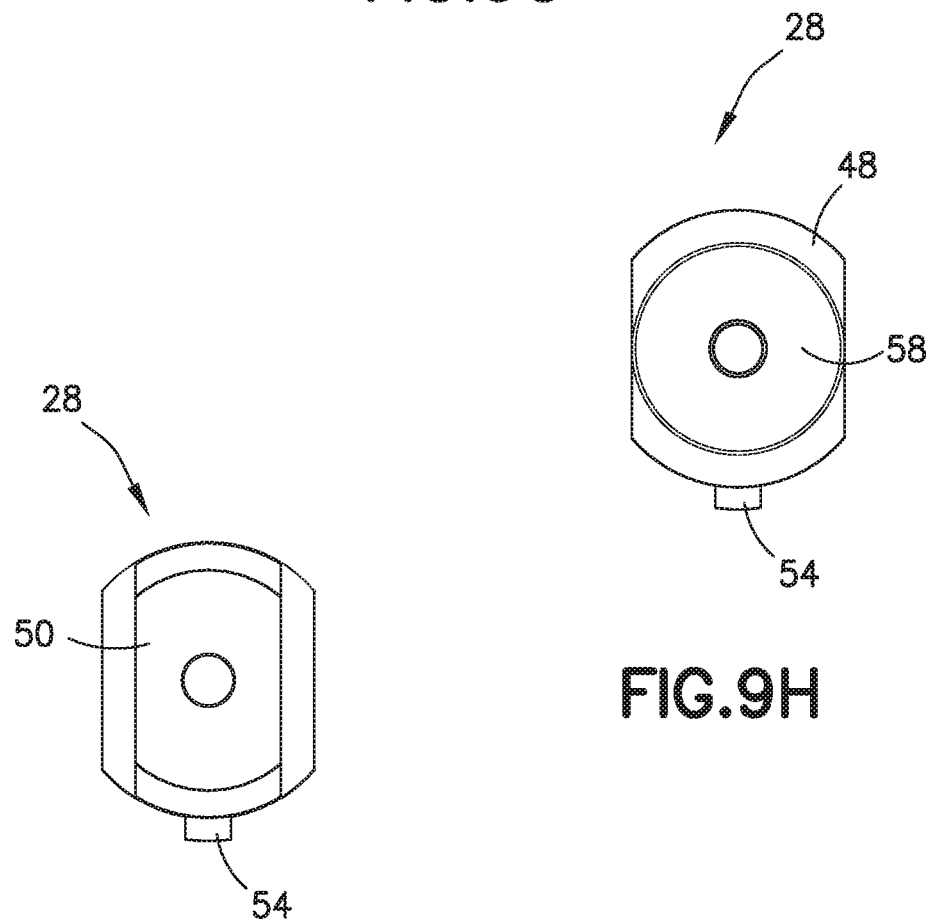
FIG.9H
FIG.9I

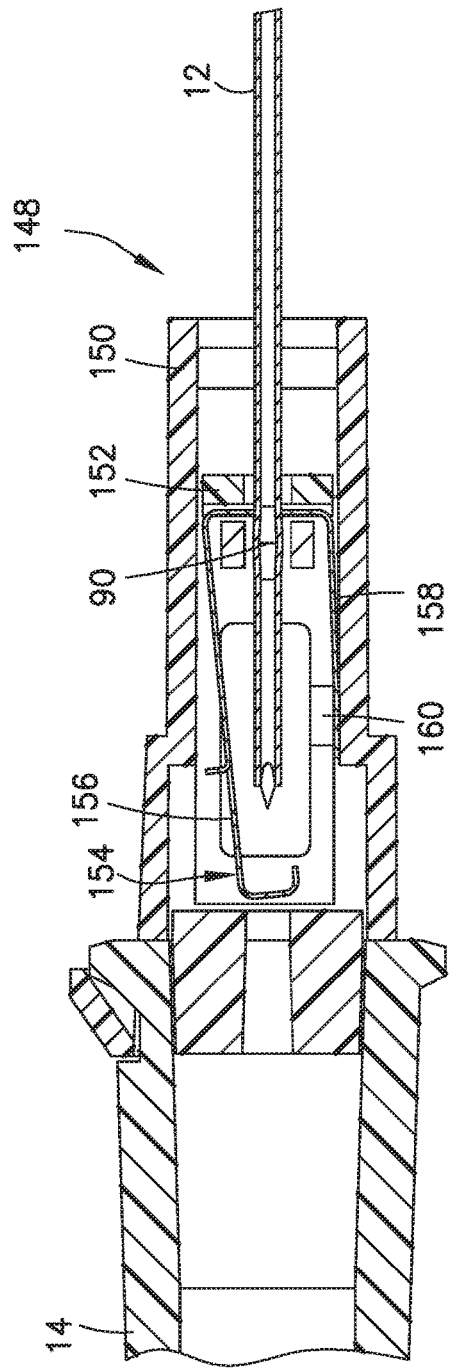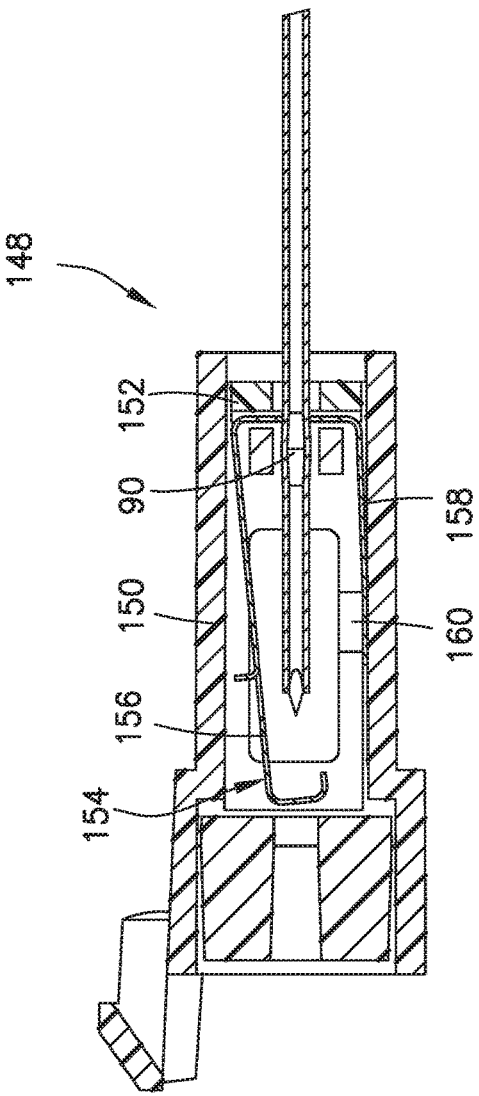

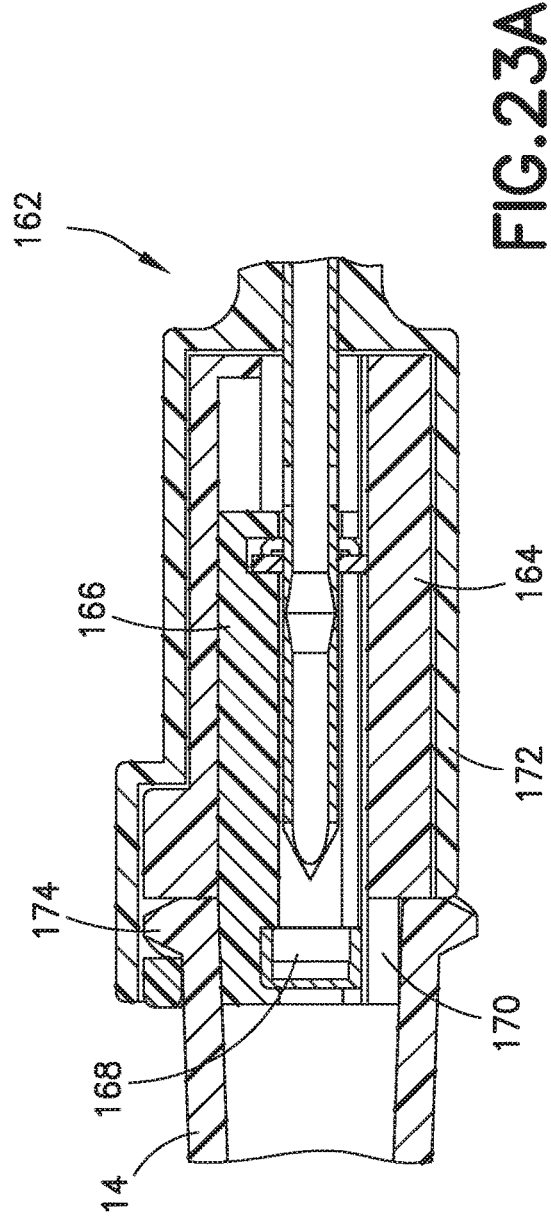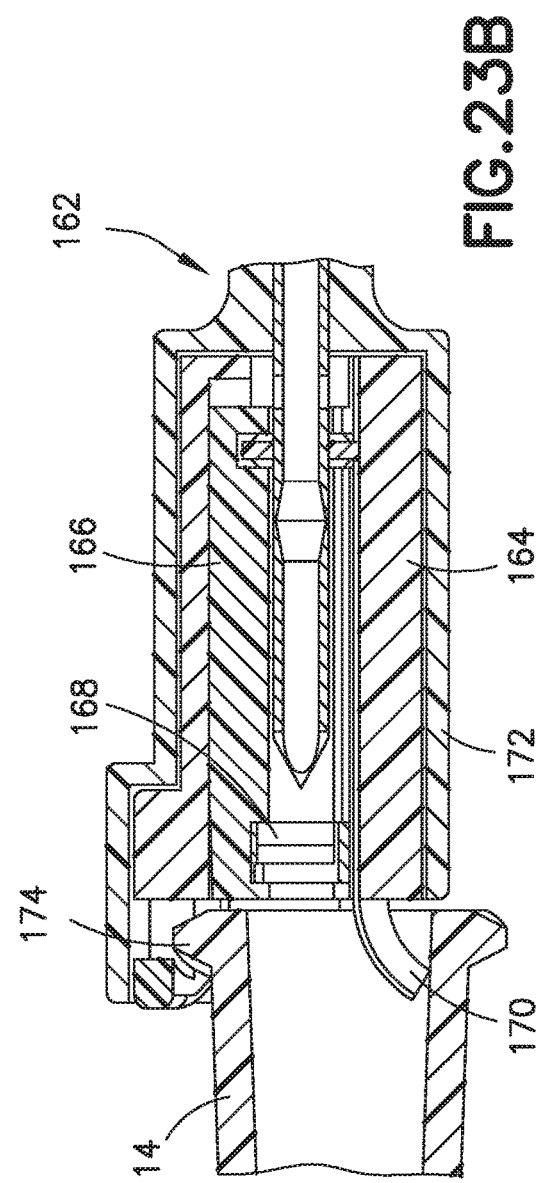

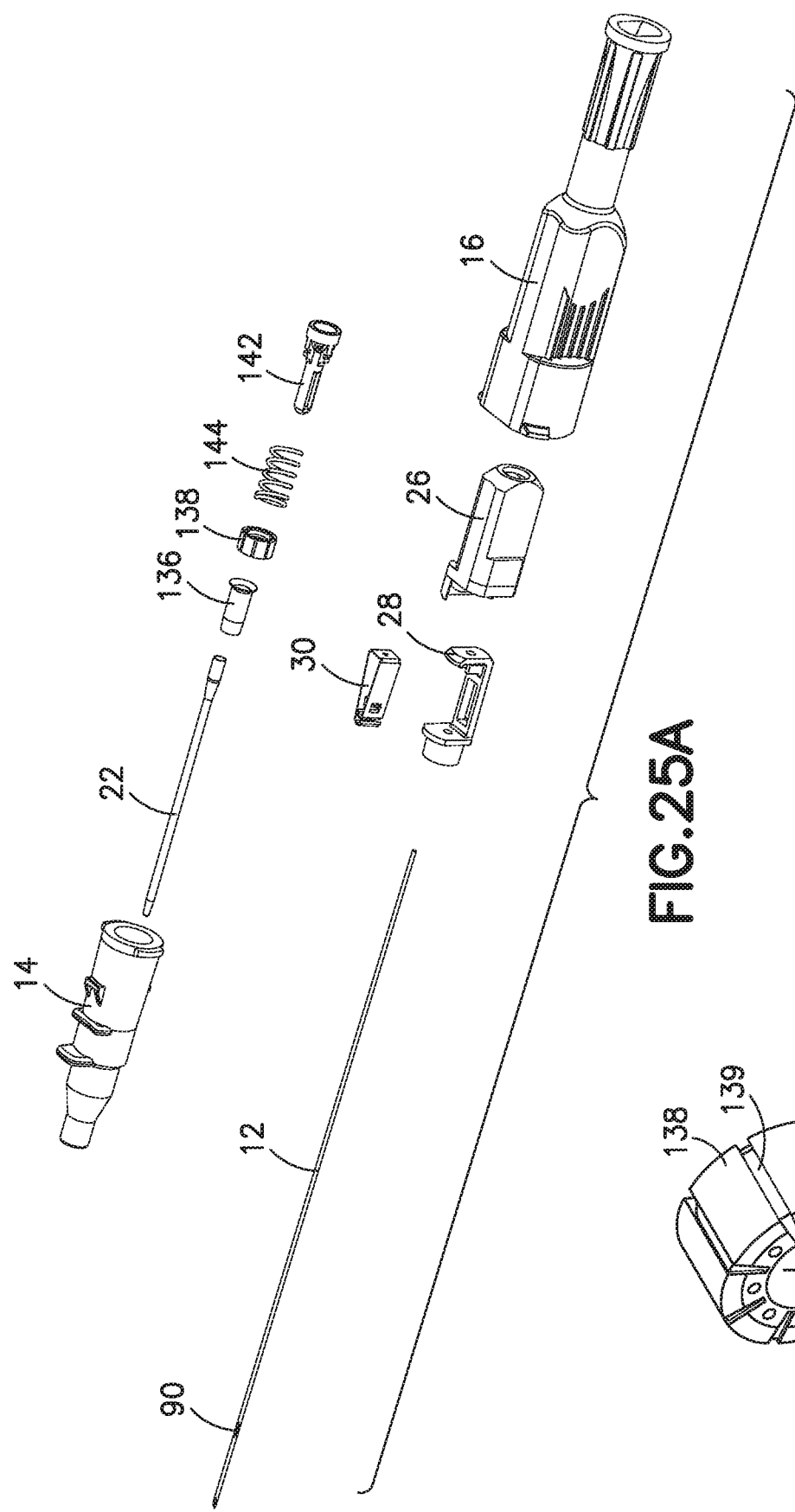

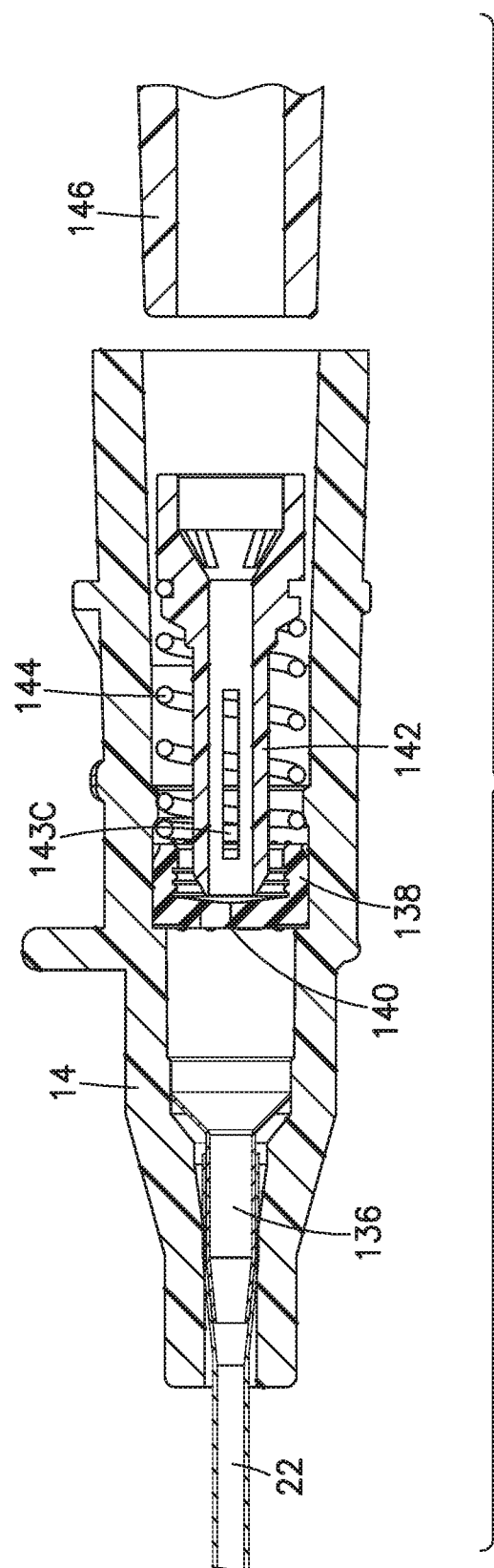

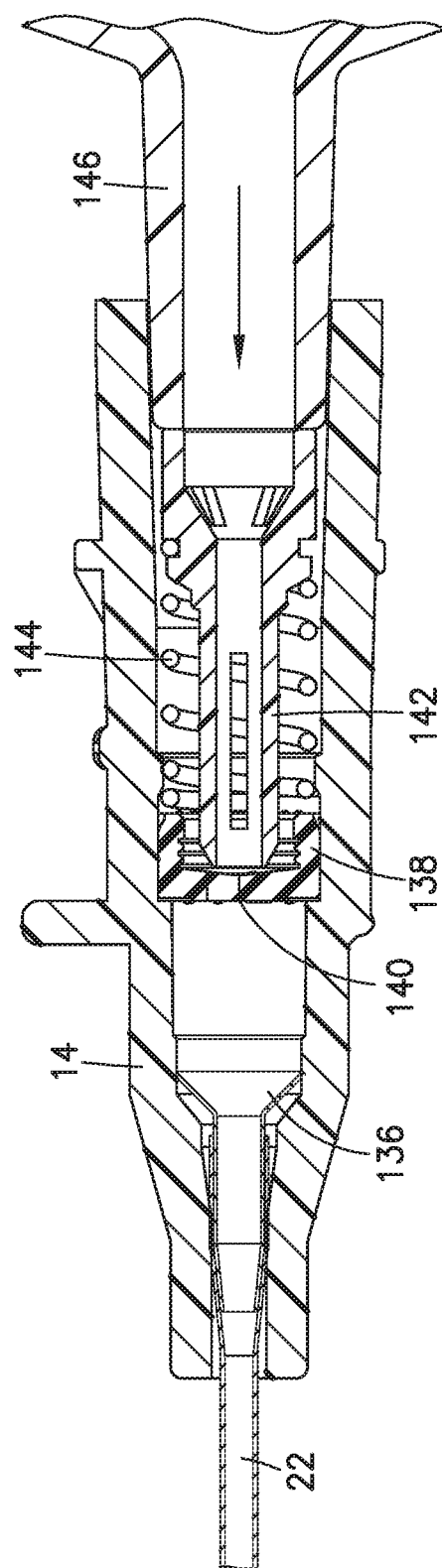

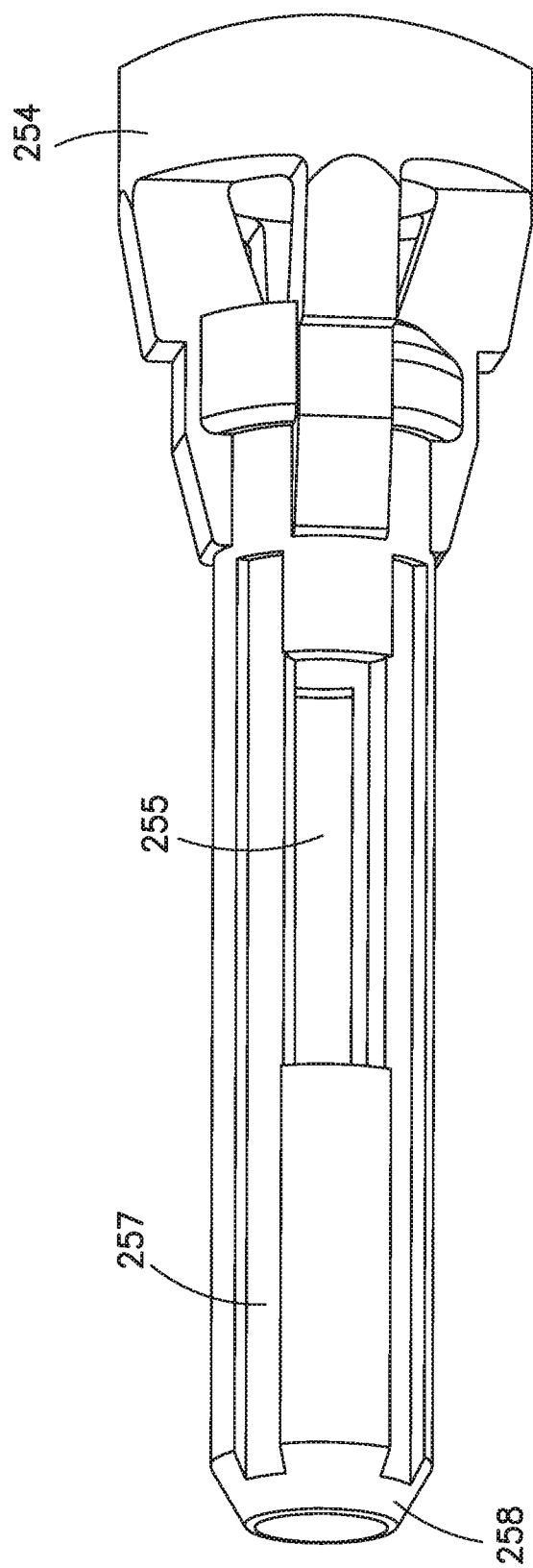

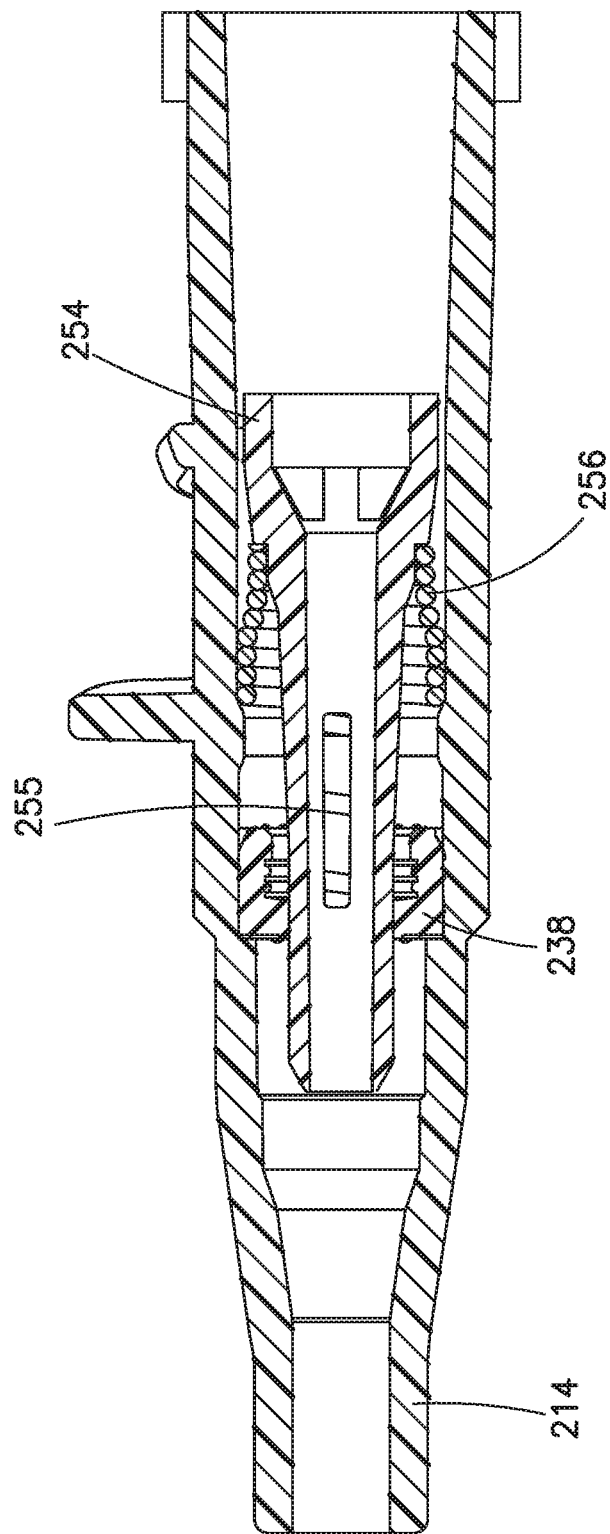

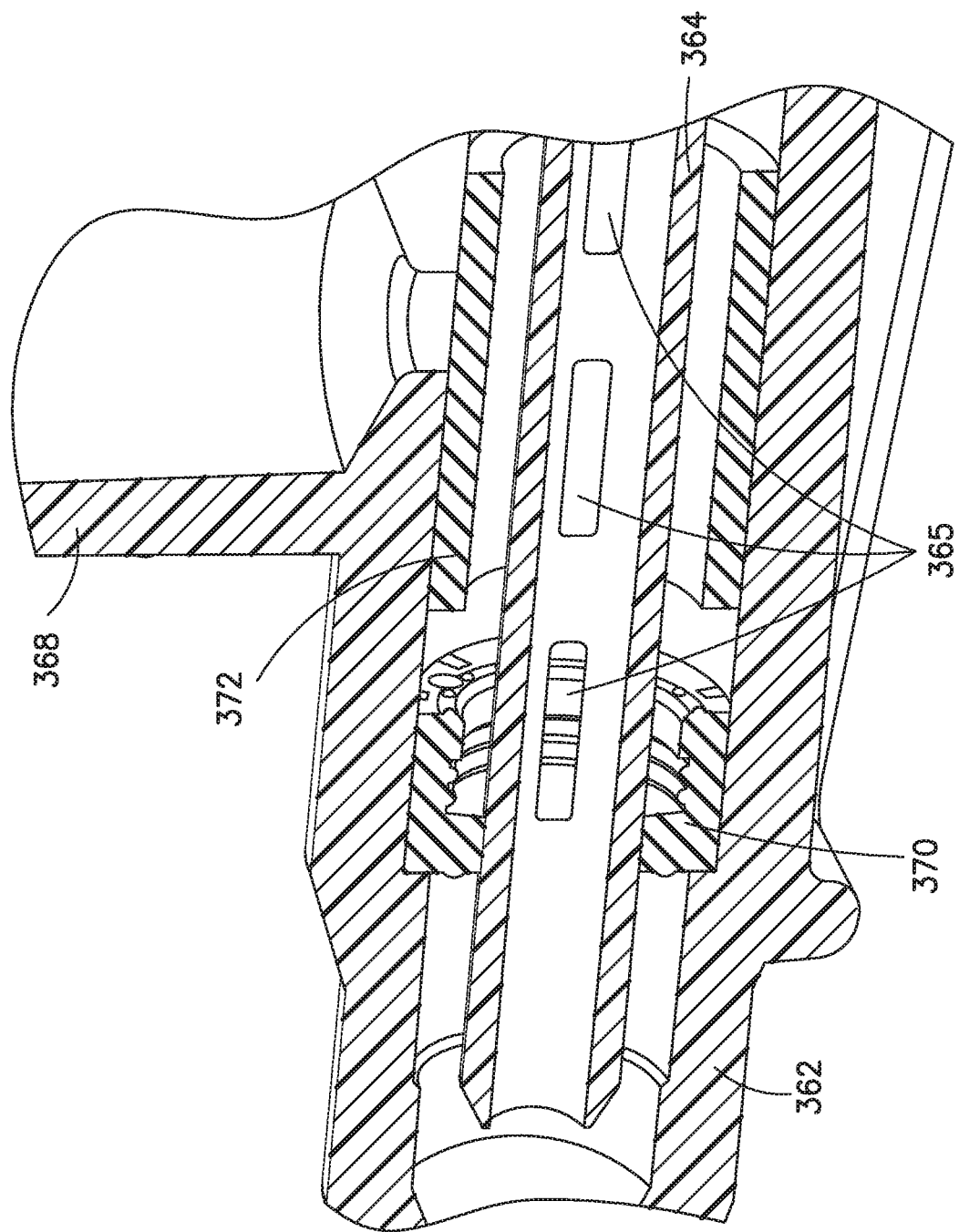

NEEDLE CAPTURE SAFETY INTERLOCK FOR CATHETER

RELATED APPLICATIONS

This application is a continuation of U.S. Nonprovisional application Ser. No. 15/304,332, filed Oct. 14, 2016, which is a national stage application, filed under 35 U.S.C. § 371, of International Application No. PCT/US2015/026536, filed Apr. 17, 2015, which claims the benefit under 35 U.S.C. § 119(e) of U.S. Provisional Application Ser. 61/981,223, filed on Apr. 18, 2014, U.S. Provisional Application 61/981,312, filed on Apr. 18, 2014, and U.S. Provisional Application Ser. No. 62/077,760, filed on Nov. 10, 2014. Each of these applications is hereby incorporated by reference in its entirety.

FIELD

Various exemplary embodiments of the invention relate to catheters.

BACKGROUND

Catheter assemblies are used to place a catheter properly into the vascular system of a patient. Once in place, catheters such as intravenous catheters may be used to infuse fluids including normal saline, medicinal compounds, and/or nutritional compositions into a patient in need of such treatment. Catheters additionally enable the removal of fluids from the circulatory system and monitoring of conditions within the vascular system of the patient.

SUMMARY OF THE INVENTION

It is an aspect of the present invention to provide a catheter assembly in which a clip provides needle protection but does not interlock the catheter hub to the needle shield. Instead, the catheter assembly incorporates an outer needle member, an inner needle member and a clip disposed in the inner needle member. The outer member interlocks the catheter hub based on the engagement of the opposing member in the inner member to a bore of the catheter hub. The needle protection arrangement can be used with existing catheter hubs and does not require any special features to be provided on the outside or inside of the catheter hub.

The foregoing and/or other aspects of the present invention can be achieved by providing a catheter assembly comprising a flexible catheter, a needle having a sharp distal tip, the needle disposed in the flexible catheter and moving from a first position that exposes the needle to a second position, an outer member that is configured to engage and disengage a catheter hub, an inner member disposed in the outer member, and a needle protection member disposed in the inner member, the needle protection member encloses at least a portion of the needle when the needle is in the second position.

The foregoing and/or other aspects of the present invention can further be achieved by providing a catheter assembly comprising a flexible catheter, a needle having a sharp distal tip, the needle disposed in the flexible catheter and moving from a first position that exposes the needle to a second position, an outer member configured to engage and disengage a catheter hub, an inner member disposed in the outer member, the inner member having an opposing member that engages the catheter hub when the needle is in the first position, and a needle protection member disposed in the inner member that encloses at least a portion of the needle when the needle is in the second position, wherein when the needle is in the second position, the inner member axially moves relative to the outer member causing the opposing member to disengage the catheter hub and allowing the outer member to disengage from the catheter hub.

The foregoing and/or other aspects of the present invention can also be achieved by providing a method of operating a catheter assembly comprising disposing a needle having a sharp distal tip in a flexible catheter and in a first position configured to receive blood, retracting the needle while maintaining blood flow through the flexible catheter, enclosing at least a portion of the needle by a needle protection member in a second position, and moving the needle protection member that is disposed in an inner member when retracting the needle in the second position which causes the inner member to axially move inside of an outer member and permits the outer member to disengage the catheter hub.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which:

FIG. 6 is an exploded, perspective view of an exemplary needle, needle shield, and needle hub;

FIG. 9G is a bottom view of the inner sleeve of FIG. 6;
FIG. 9H is a front view of the inner sleeve of FIG. 6;
FIG. 9I is a rear view of the inner sleeve of FIG. 6.

FIG. 22B is the needle shield and catheter hub of FIG. 22A with the needle drawn into the outer sleeve;

FIG. 22C is the needle shield of FIG. 22A separated from the catheter hub;

FIG. 23A is a sectional, side view of another exemplary embodiment of a needle shield connected to a catheter hub;

FIG. 23B is the needle shield of FIG. 23A with the inner sleeve withdrawn from the catheter hub and a biasing member disengaging the catch;

FIG. 25A is an exploded, perspective view of an exemplary catheter having a needle shield and a spring-return blood control actuator and septum;

FIG. 25B is a perspective view of the septum of FIG. 25A;

FIG. 26B is a sectional, side view of the catheter of FIG. 26A with the needle removed;

FIG. 26C is a sectional, side view of the catheter of FIG. 26B with a male Luer connector inserted into the catheter hub;

FIG. 27 illustrates a right side view of another exemplary embodiment of an actuator;

FIG. 28B illustrates the cross sectional view of the catheter hub assembly of FIG. 28A when piercing a septum;

FIG. 29C illustrates a left perspective cross sectional view of the catheter hub assembly of FIG. 29A when piercing a septum.

DETAILED DESCRIPTION OF EXEMPLARY EMBODIMENTS

Figure 1:
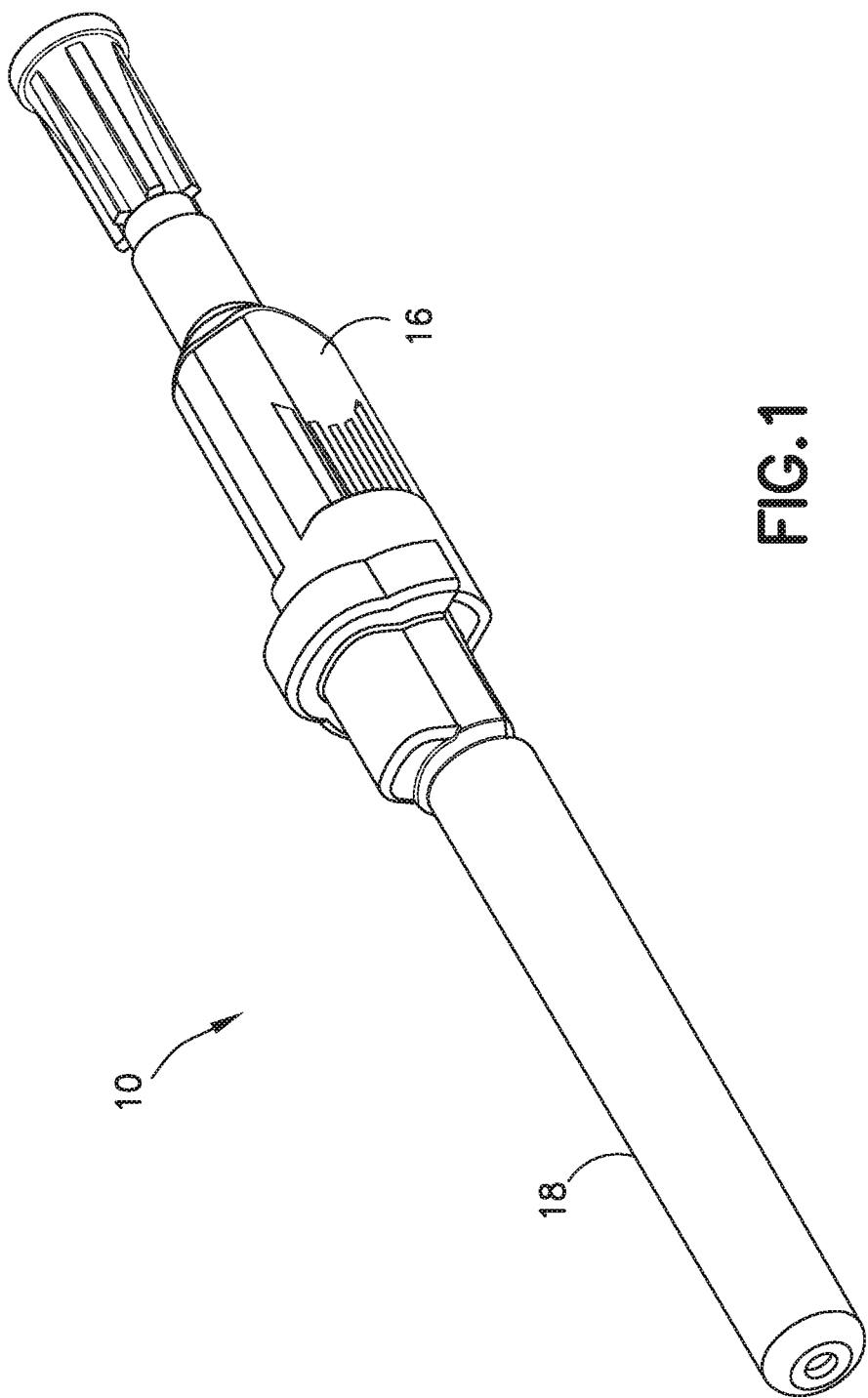
FIG. 1 is a perspective view of an exemplary catheter with a needle cover attached.
Figure 2:
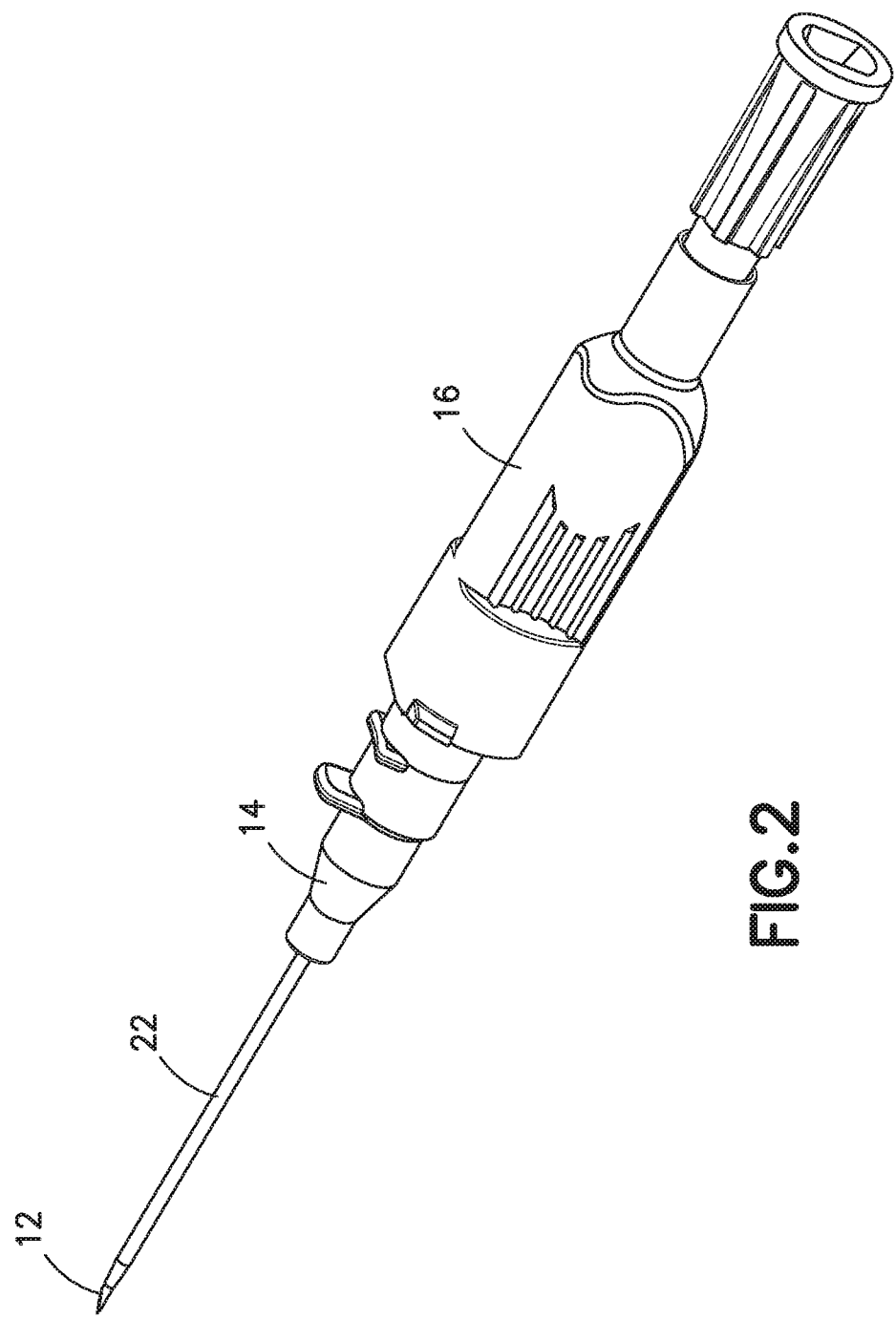
FIG. 2 is a perspective view of the catheter of FIG. 1 with the needle cover removed.
Figure 3:
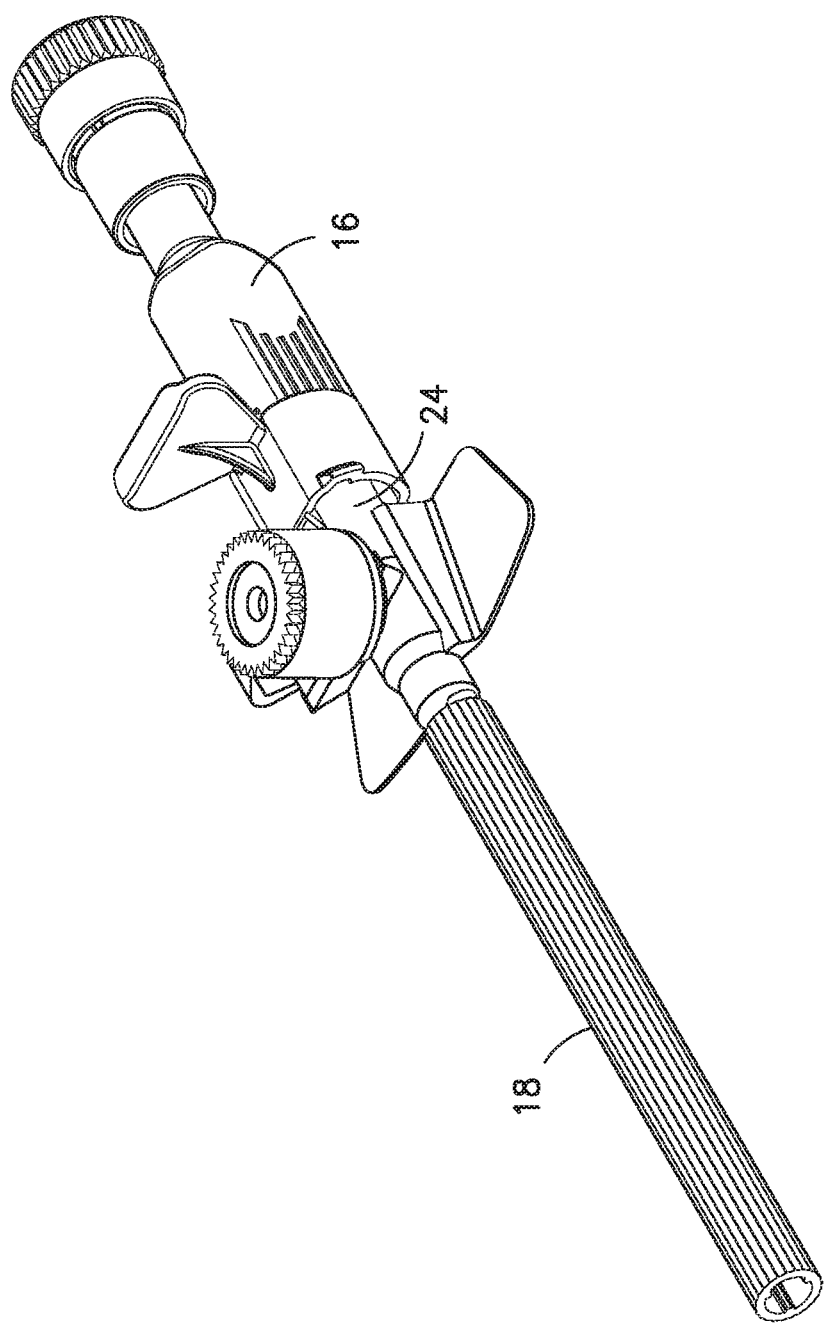
FIG. 3 is a perspective view of an exemplary side-port catheter and needle cover.
Figure 4:
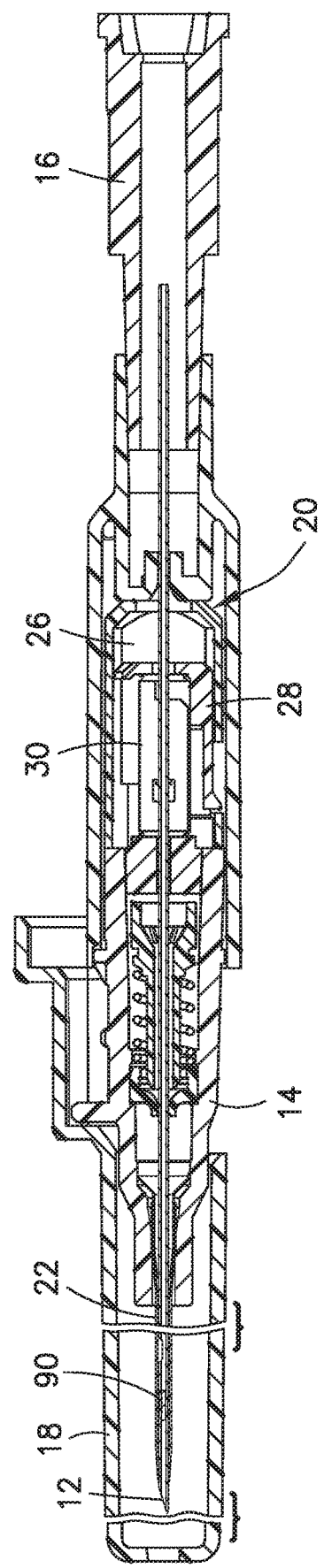
FIG. 4 is a sectional, side view of the catheter of FIG. 1.
Figure 5:
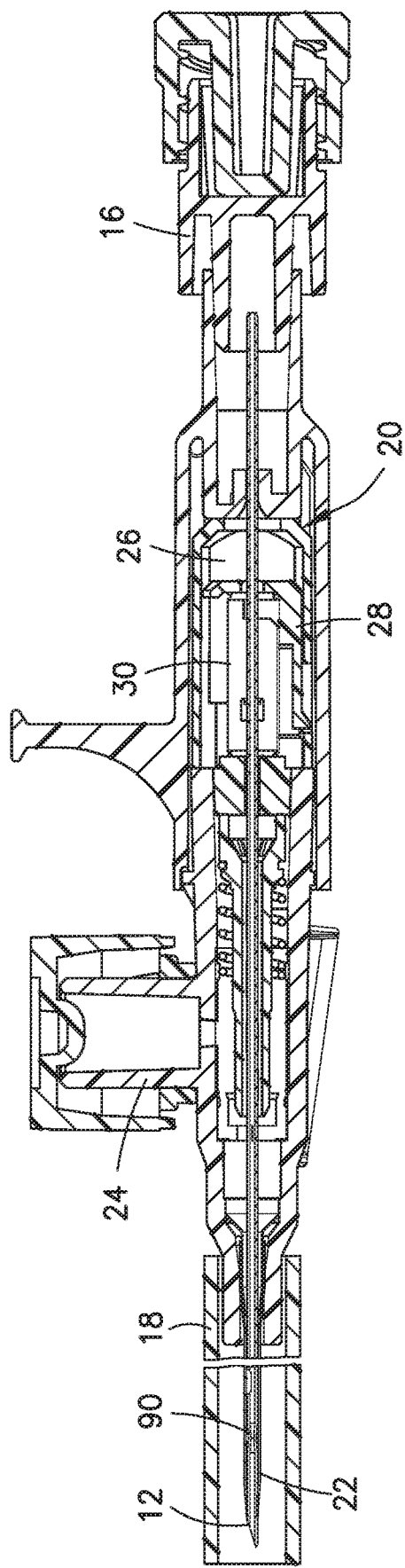
FIG. 5 is a sectional, side view of the catheter of FIG. 3.
Figure 7A:
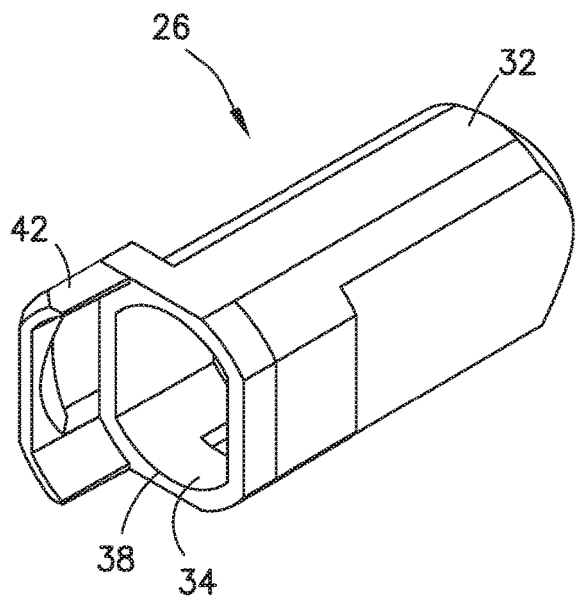
FIGS. 7A-D are perspective views of the outer sleeve of the exemplary needle shield of FIG. 6.
Figure 7B:
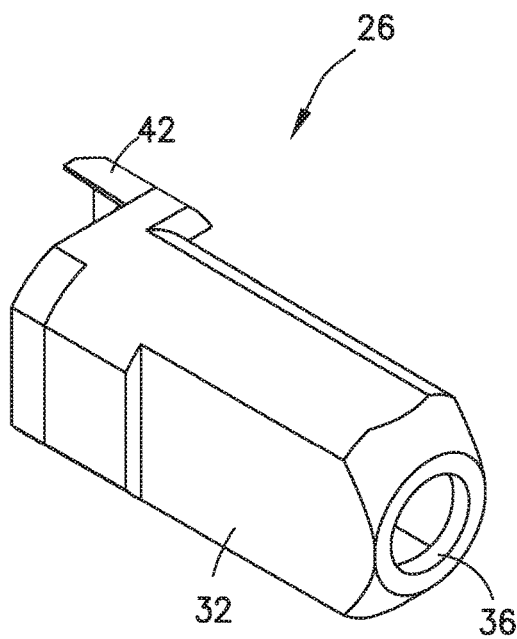
Figure 7C:
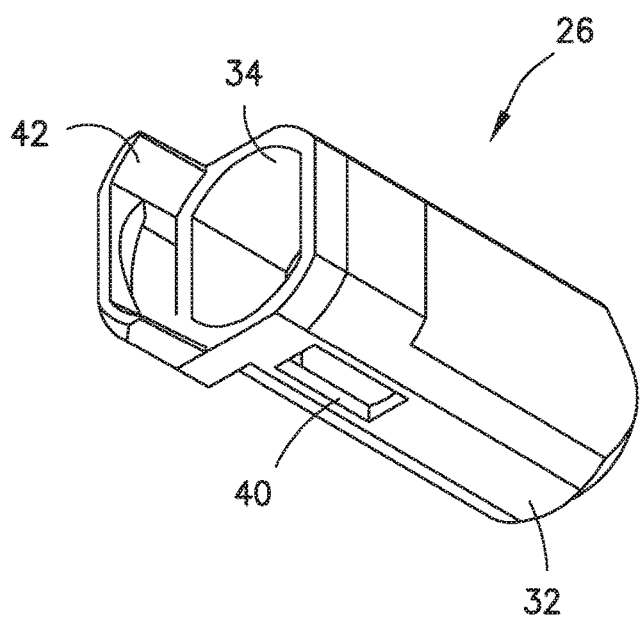
Figure 7D:
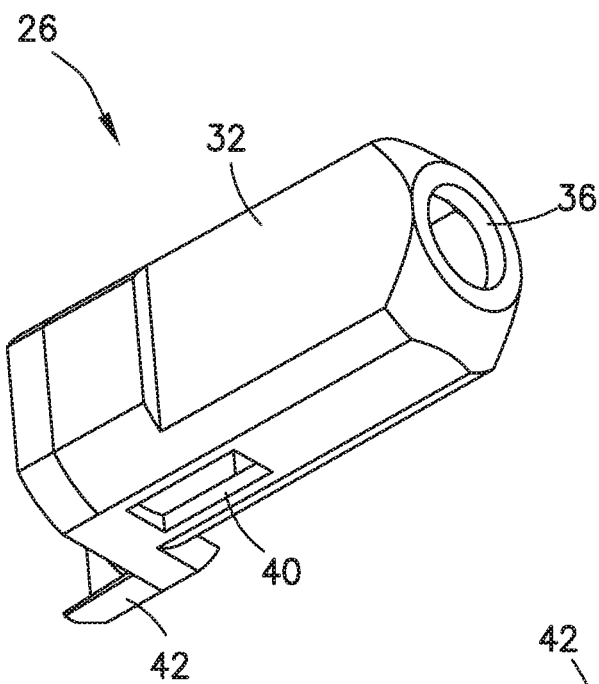
Figure 7E:
FIG. 7E is a top view of the outer sleeve of FIG. 6.
Figure 7F:
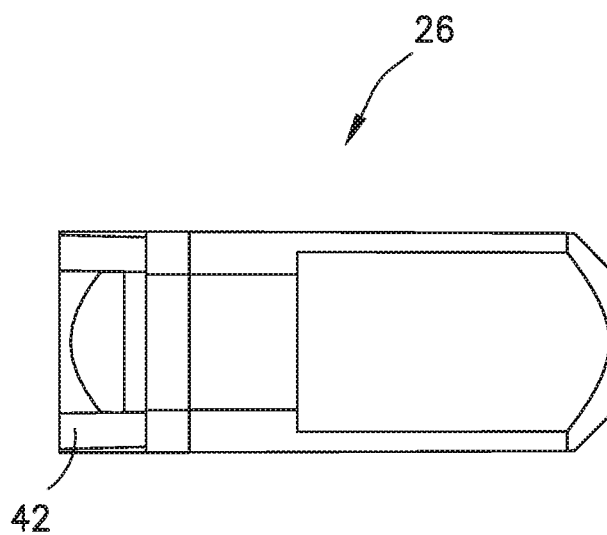
FIG. 7F is a right side of the outer sleeve of FIG. 6.
Figure 7G:
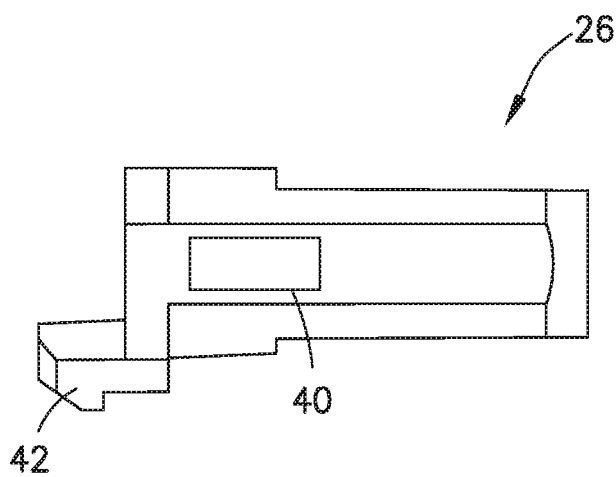
FIG. 7G is a bottom view of the outer sleeve of FIG. 6.
Figure 7H:
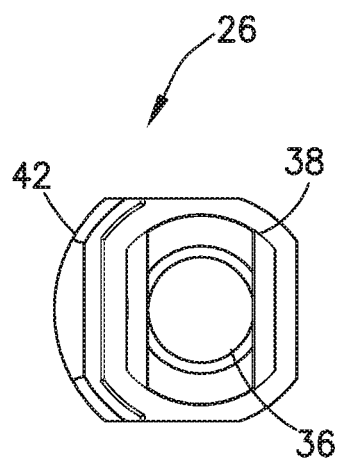
FIG. 7H is a front view of the outer sleeve of FIG. 6.
Figure 7I:
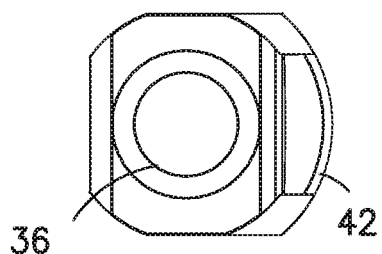
FIG. 7I is a rear view of the outer sleeve of FIG. 6.
Figure 7J:
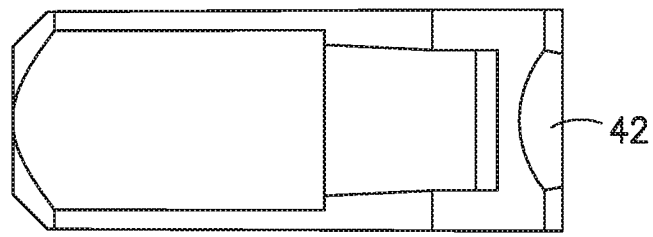
FIG. 7J is a left side view of the outer sleeve of FIG. 6.

A catheter 10, as illustrated in FIGS. 1-6, includes a hollow metal introducer needle 12, a catheter hub 14, a needle hub 16, a needle cover 18, and a needle shield 20. The needle cover 18 initially covers the needle 12 and at least a portion of the catheter hub 14. The needle cover 18 can connect to the catheter hub 14 or to the needle hub 16. The needle 12 has a sharpened distal end and initially extends through the needle shield 20 and the catheter hub 14. A flexible catheter tube 22 extends from the distal end of the catheter hub 14, with the introducer needle 12 passing through the catheter tube 22. Initially, the needle 12 is exposed (first position, for example) and is inserted into a patient's vein. The catheter tube 22 is pushed along the needle 12 and into the vein following the needle 12. After the catheter tube 22 is inserted, the needle 12 is removed from the patient's vein and the catheter hub 14. The needle shield 20 encloses the sharp distal tip of the needle 12 and provides protection from being stuck by the needle 12 during and after the needle's retraction from the catheter hub 14. The needle shield 20 can be used with a variety of different catheters, including standard catheter hubs 14 as shown in FIGS. 2 and 4 and side-port catheter hubs 24 as shown in FIGS. 3 and 5.

In accordance with various exemplary embodiments, the needle shield 20 includes an outer member 26, an inner member 28, and a resilient clip 30. The outer and inner members 26, 28 are preferably in the form of sleeves. The outer sleeve 26 connects to the catheter hub 14 and surrounds the inner sleeve 28, and the clip 30. The inner sleeve 28 is positioned in the outer sleeve 26 and is moveable in the axial direction relative to the outer sleeve 26. The clip 30 is connected to, and axially moveable with, the inner sleeve 28. The outer sleeve 26, inner sleeve 28, and clip 30 may be formed from a metal, elastomer, polymer, or composite material. In various exemplary embodiments, the outer sleeve 26 and the inner sleeve 28 are molded from a polymer material and the clip 30 is formed from a thin piece of resilient metal, such as stainless steel. The clip in the various embodiments disclosed can act as an exemplary needle protection member. The features of the exemplary embodiments of FIGS. 1-6 may be combined with features of the other exemplary embodiments disclosed herein as appropriate.

In accordance with the exemplary embodiments depicted in FIGS. 7A-7J, the outer sleeve 26 includes an outer surface 32, an inner surface 34, a proximal opening 36, and a distal opening 38. The outer surface 32 has an octagonal configuration with eight planar sides, although other curvilinear and/or rectilinear shapes may be used. The inner surface 34 has a planar top wall and a planar bottom wall connected by a pair of curved sides. The inner surface 34 defines a cavity for receiving the inner sleeve 28. The introducer needle 12 initially extends through the proximal and distal openings. A slot 40 extends through a wall of the outer sleeve 26. The size, shape, and configuration of the outer sleeve may vary depending on space requirements and the type of catheter hub 14.

Figure 8A:
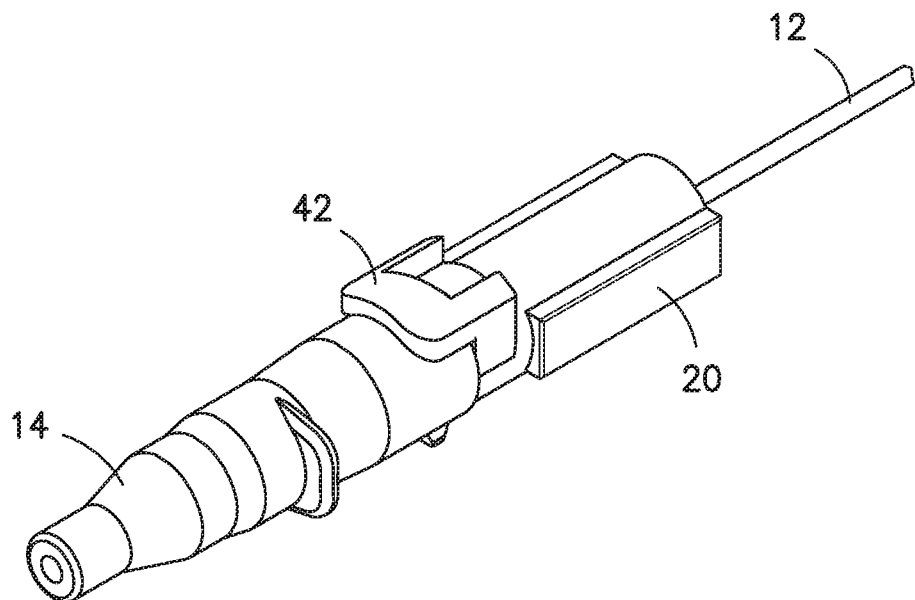
FIG. 8A is a perspective view of the needle shield connected to the catheter hub.
Figure 8B:
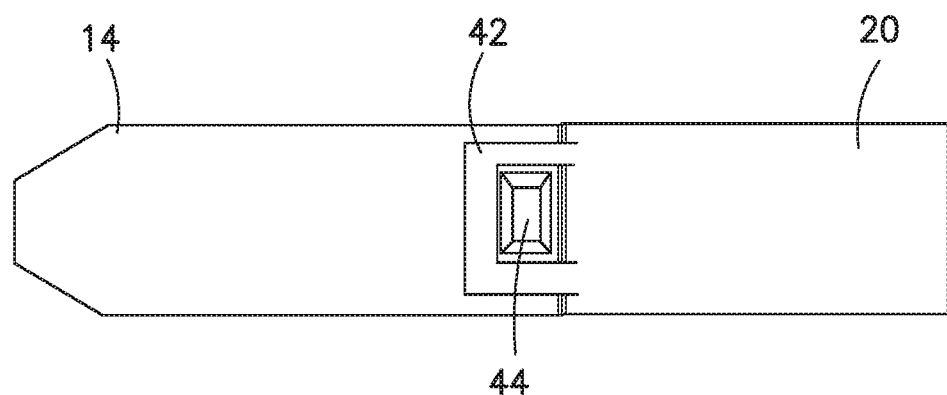
FIG. 8B is a top view of the needle shield connected to the catheter hub.
Figure 9A:
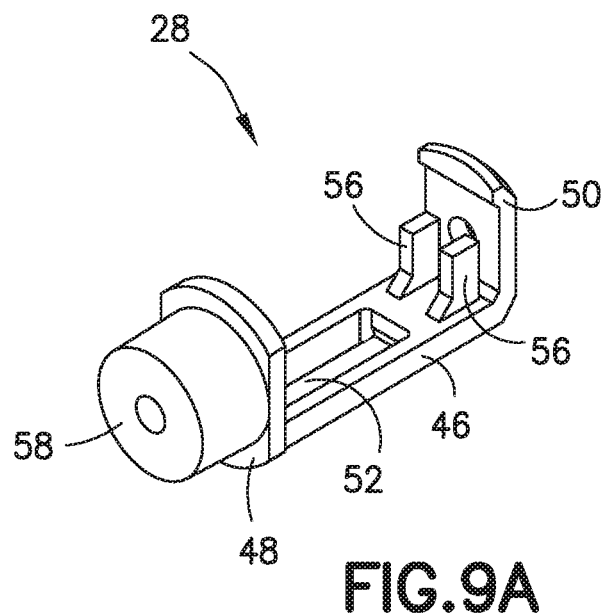
FIGS. 9A-D are perspective views of the inner sleeve of the exemplary needle shield of FIG. 6.
Figure 9B:
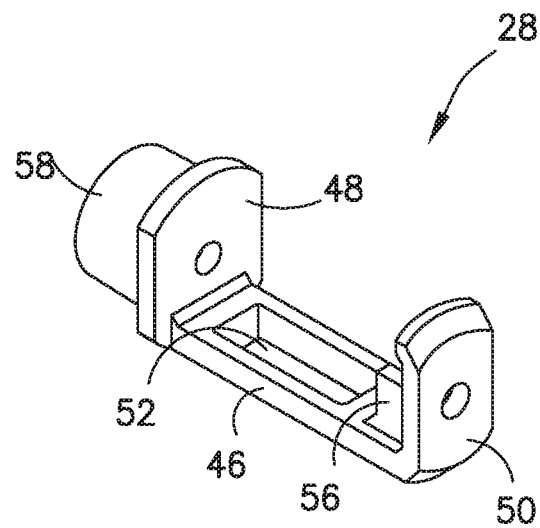
Figure 9C:
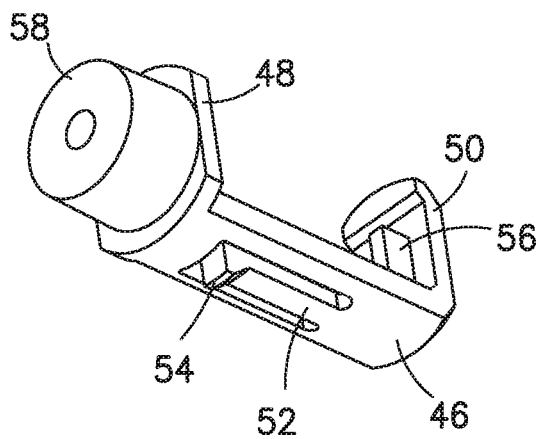
Figure 9D:
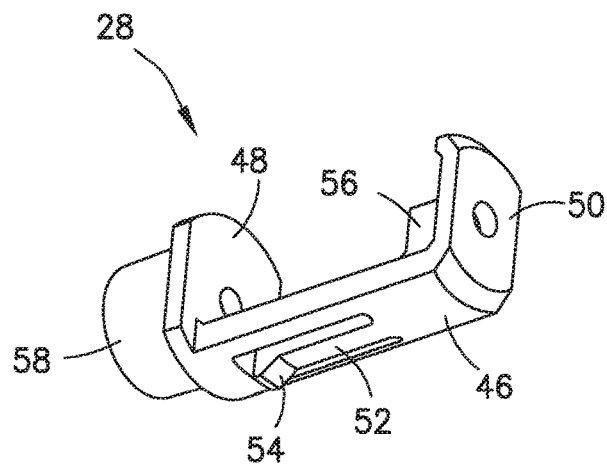
Figure 9E:
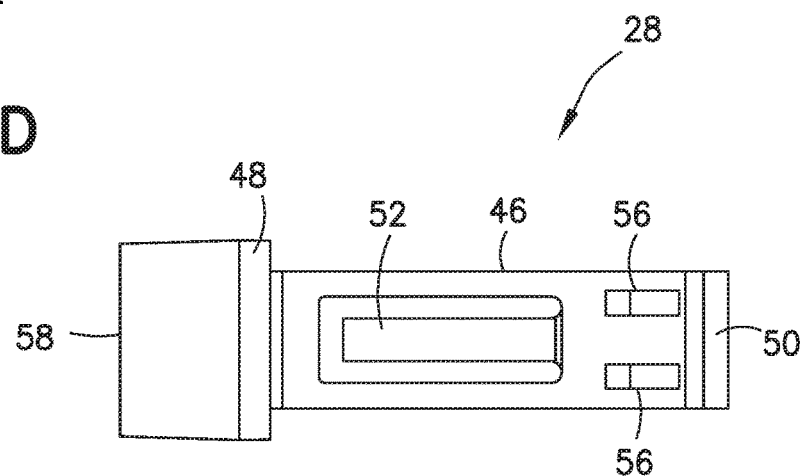
FIG. 9E is a top view of the inner sleeve of FIG. 6.
Figure 9F:
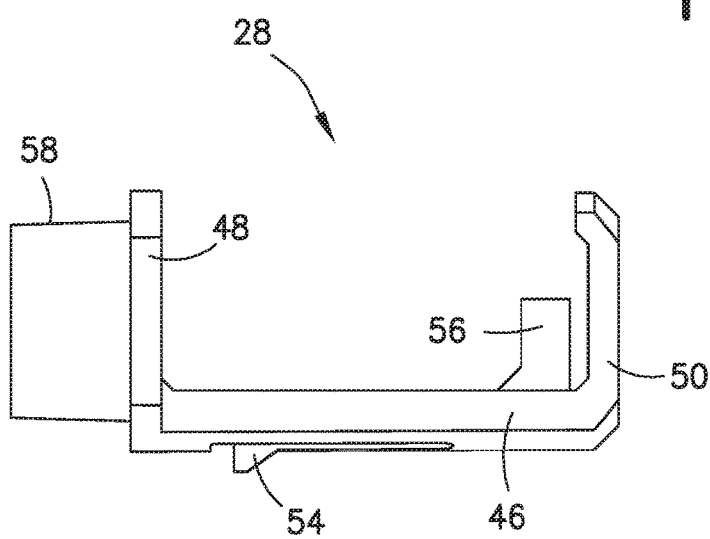
FIG. 9F is a right side view of the inner sleeve of FIG. 6.
Figure 10A:
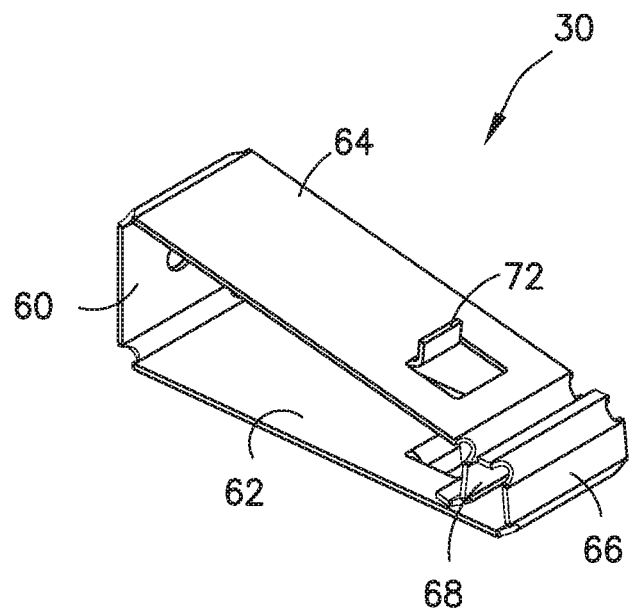
FIGS. 10A-D are perspective views of the clip of the exemplary needle shield of FIG. 6.
Figure 10B:
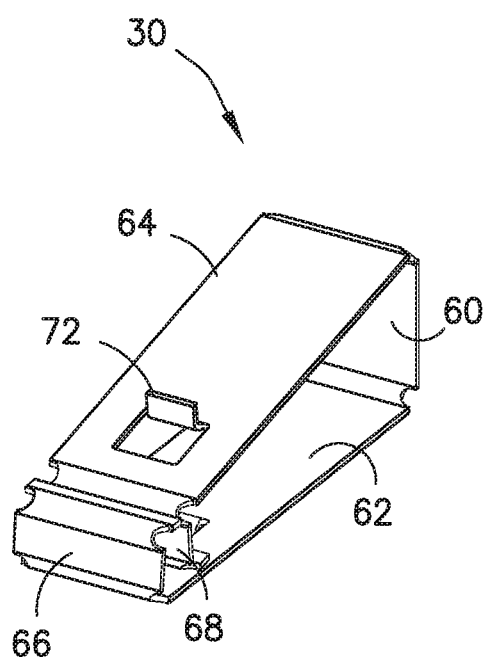
Figure 10C:
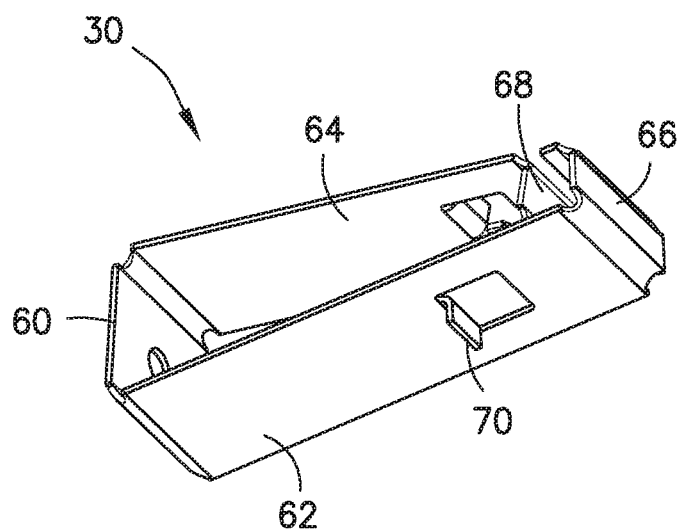
Figure 10D:
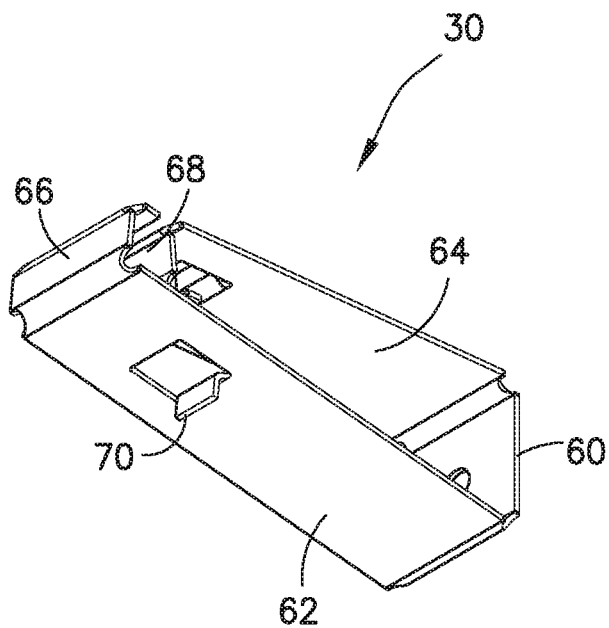
Figure 10E:
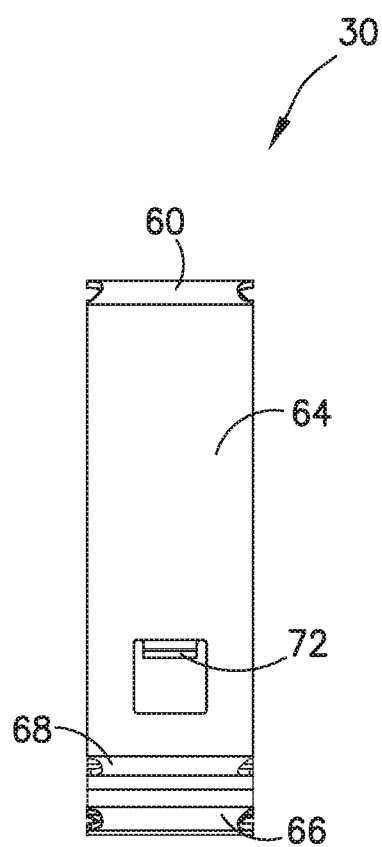
FIG. 10E is a right side view of the clip of FIG. 6.
Figure 10F:
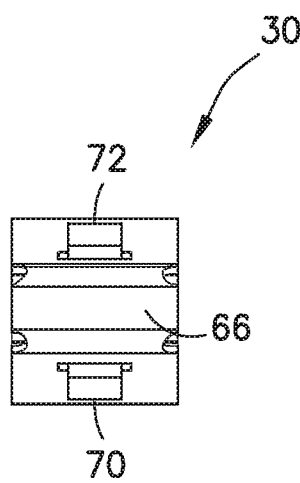
FIG. 10F is a front view of the clip of FIG. 6.
Figure 10G:
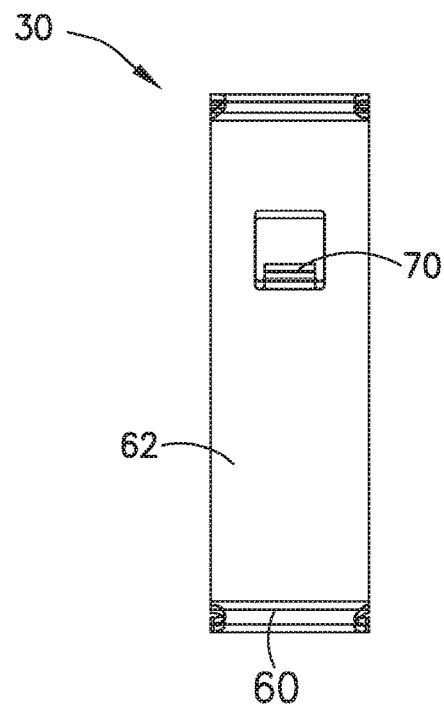
FIG. 10G is a left side view of the clip of FIG. 6.
Figure 10H:
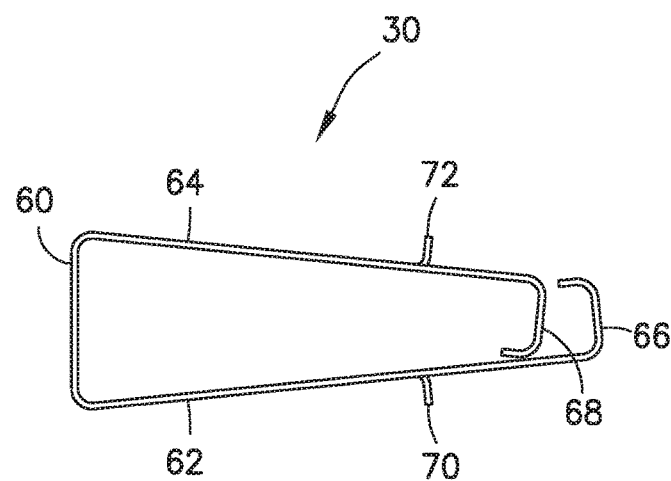
FIG. 10H is a top view of the clip of FIG. 6.
Figure 10I:
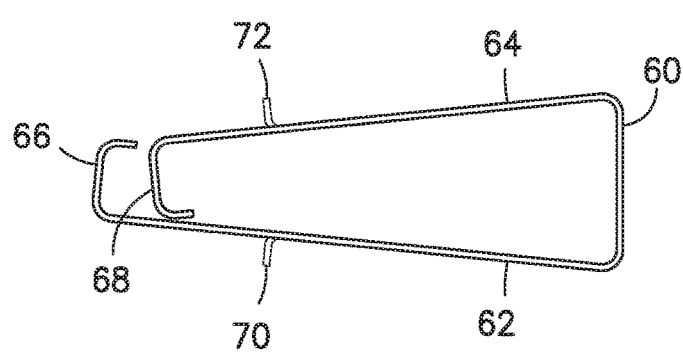
FIG. 10I is a bottom view of the clip of FIG. 6.

A catch 42 extends from the outer surface to engage or interlock with a protrusion 44 on the catheter hub 14 as best shown in FIGS. 8A-8B. This engagement takes place prior to the needle 12 being enclosed by the clip 30. In various exemplary embodiments the catch 42 may be configured to engage any type of feature on the catheter hub 14, including a groove, slot, or hole. Modification of the catch 42 may be dependent on the configuration of the catheter hub 14. In the exemplary embodiment, the catheter hub protrusion 44 is a Luer receiving thread, for example a LUER-LOK® style of thread.

The catch 42 has a front edge, a back edge, and a pair of side edges. An opening or depression is formed between the front edge and the back edge to receive the catheter hub protrusion 44. The opening allows the catch 42 to be formed with a clearance approximately equal to, or slightly greater than the height of the projection 44, allowing the catch 42 to engage the front, back, and/or sides of the Luer thread projection 44 while minimizing the amount of material and space needed. In various exemplary embodiments, the opening may be omitted. The catch 42 resists premature release of the needle shield 20 from the catheter hub 14. The features of the exemplary embodiments of FIGS. 7A-8B may be combined with features of the other exemplary embodiments disclosed herein as appropriate.

In accordance with the exemplary embodiments depicted in FIGS. 9A-9I, the inner sleeve 28 includes a base 46, a distal side 48, and a proximal side 50. A resilient leg 52 and a foot 54 extend from an outer surface of the base 46. The resilient leg 52 and the foot 54 engage the slot 40 in the outer sleeve 26. One or more clip retainers 56 extend from an inner surface of the base 46. The clip 30 is positioned between the clip retainers 56 and the proximal side 50. An opposing member 58 extends from the distal side 48 in the distal direction. The opposing member 58 is configured to be inserted into the catheter hub 14 when the needle 12 is in the exposed position (first position, for example). In the exemplary embodiment shown in FIG. 9A-9I the opposing member is a tubular member. The proximal side 50, distal side 48, and opposing member 58 each has an opening for receiving the introducer needle 12. The size, shape, and configuration of the inner sleeve 28 may vary depending on space requirements and the type of catheter hub 14, and outer sleeve 26.

In an alternate embodiment of the inner sleeve 18, a bridge member (not shown) can be incorporated to improve the strength of the inner sleeve 18. Specifically, the top surface of the distal side 48 and the top surface of the proximal side 50 can be connected by a solid member having a similar length of the base 46. The inner sleeve 18 can be manufactured by injection molding, for example.

In another alternate embodiment, the foot 54 of the base 46 can be removed and the base 46 can be a solid member. According to this configuration, the inner sleeve 28 deforms in the outer sleeve 26 to achieve appropriate retention. The inner and outer sleeves 28, 26 are appropriately sized so that the inner sleeve 28 can also axially move inside and relative to the outer sleeve 26 upon applying a predetermined force. If a force less than the predetermined force is applied, the inner sleeve 28 does not move relative to the outer sleeve 26. Such a configuration improves moldability and manufacturability of the inner sleeve 28 and outer sleeve 26. The features of the exemplary embodiments of FIGS. 9A-9I may be combined with features of the other exemplary embodiments disclosed herein as appropriate.

In accordance with the exemplary embodiments depicted in FIGS. 10A-10I, the resilient clip 30 includes a base 60 having an opening for receiving the needle 12, a first arm 62, and a second arm 64 extending from the base 60. The first arm 62 extends further in the axial direction than the second arm 64. The first arm 62 has a first hook 66 and the second arm 64 has a second hook 68. A first tab 70 is formed in the first arm 62 and a second tab 72 is formed in the second arm 64. The features of the exemplary embodiments of FIGS. 10A-10I may be combined with features of the other exemplary embodiments disclosed herein as appropriate.

Figure 11:
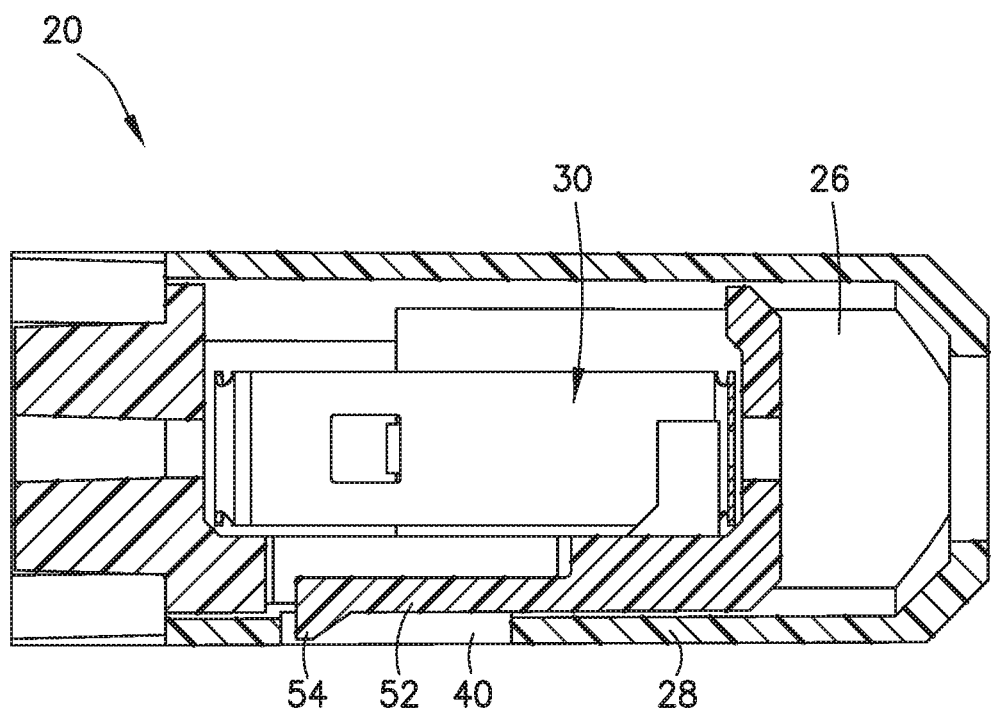
FIG. 11 is a sectional, side view of the exemplary needle shield of FIG. 6.
Figure 12:
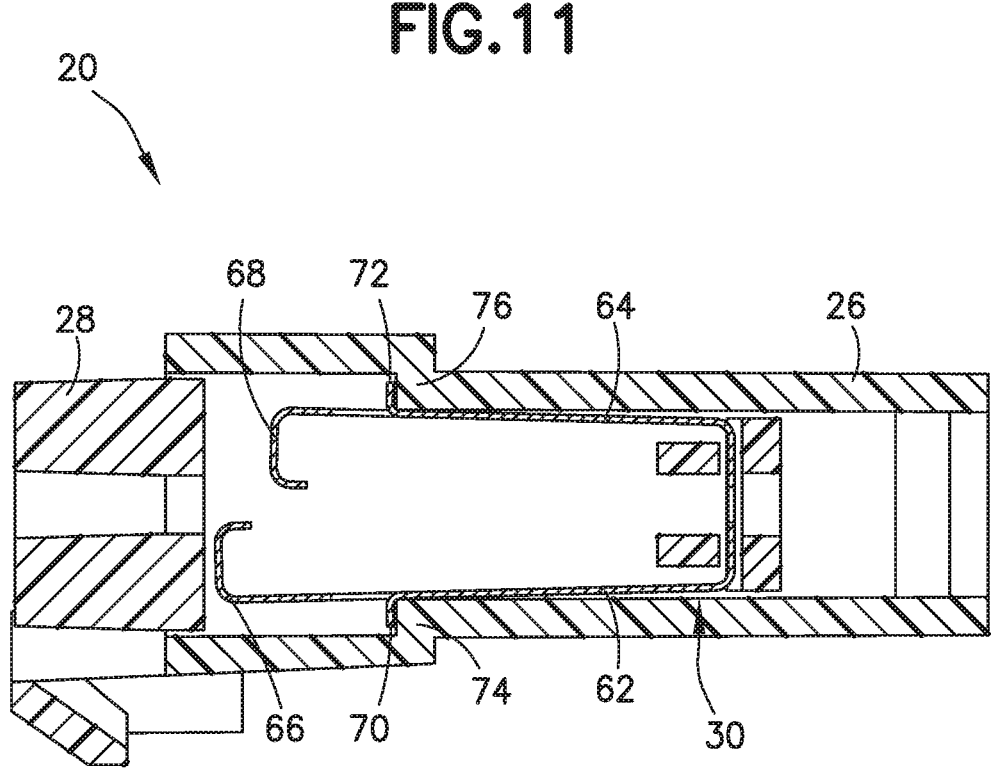
FIG. 12 is a sectional, top view of the exemplary needle shield of FIG. 6.
Figure 13:
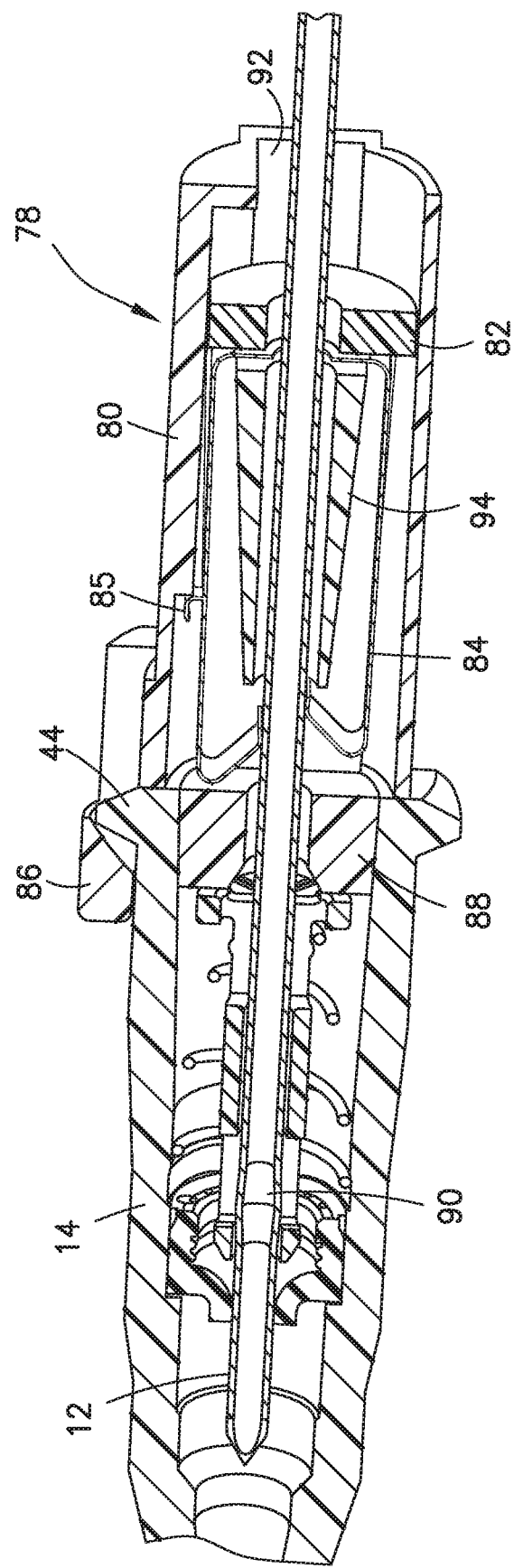
FIG. 13 is a sectional, side view of another exemplary needle shield connected to a catheter hub with an introducer needle extending into the catheter hub.

FIGS. 11 and 12 depict the exemplary embodiment of the needle shield 20 in an assembled condition. FIG. 11 shows the leg 52 and foot 54 of the inner sleeve 28 positioned in the slot 40 of the outer sleeve 26. The foot 54 engages the slot 40 to resist axial movement of the inner sleeve 28 with respect to the outer sleeve 26 past the point where the foot 54 engages an edge of the slot 40. The leg 52 and foot 54 can also be formed on the outer sleeve 26 with the slot 40 formed on the inner sleeve 28. FIG. 12 shows the first and second clip tabs 70, 72 engaging a first shoulder 74 and a second shoulder 76 on the outer sleeve 26. The tabs 70, 72 help prevent the clip 30 and the inner sleeve 28 from unintentionally sliding into the outer sleeve 26, for example during shipping. In the initial position, the introducer needle 12 biases the first and second arms 62, 64 into an open position so that the tabs 70, 72 engage the outer sleeve 26.

FIGS. 13-16 depict another example embodiment of the needle shield 78 and depict an example of the needle shield 20 in operation. Initially, the introducer needle 12 passes through the outer sleeve 80, the inner sleeve 82, and the clip 84. The introducer needle 12 biases the clip 84 into an open position, so that the first and second hooks are resting along the needle shaft 12. In the assembled position, the catch 86 engages the Luer thread 44 on the outer surface of the catheter hub 14 and the opposing member extends into the proximal opening of the catheter hub 14. In order to remove the catch 86 from the catheter hub 14, the outer sleeve 80 of the shield 78 must be raised so that the catch 86 can slide over the Luer thread 44. Raising the needle shield 78 relative to the catheter hub 14, however, is initially prevented by the opposing member 88 extending into the catheter hub 14.

As the needle 12 is withdrawn from the catheter hub 14, the tip of the needle 12 clears the first and second hooks causing the first and second arms to close and the first and second hooks to surround the tip of the needle 12. After the tip of the needle 12 passes the first and second hooks and the first and second arms move into a closed orientation, the tab 85 disengages the outer sleeve 80 and the inner sleeve 82 may be moved axially further into the outer sleeve 80. A second position can refer to the closed position, whereas the first position can refer to any needle 12 position prior to entering the second position.

Figure 14:
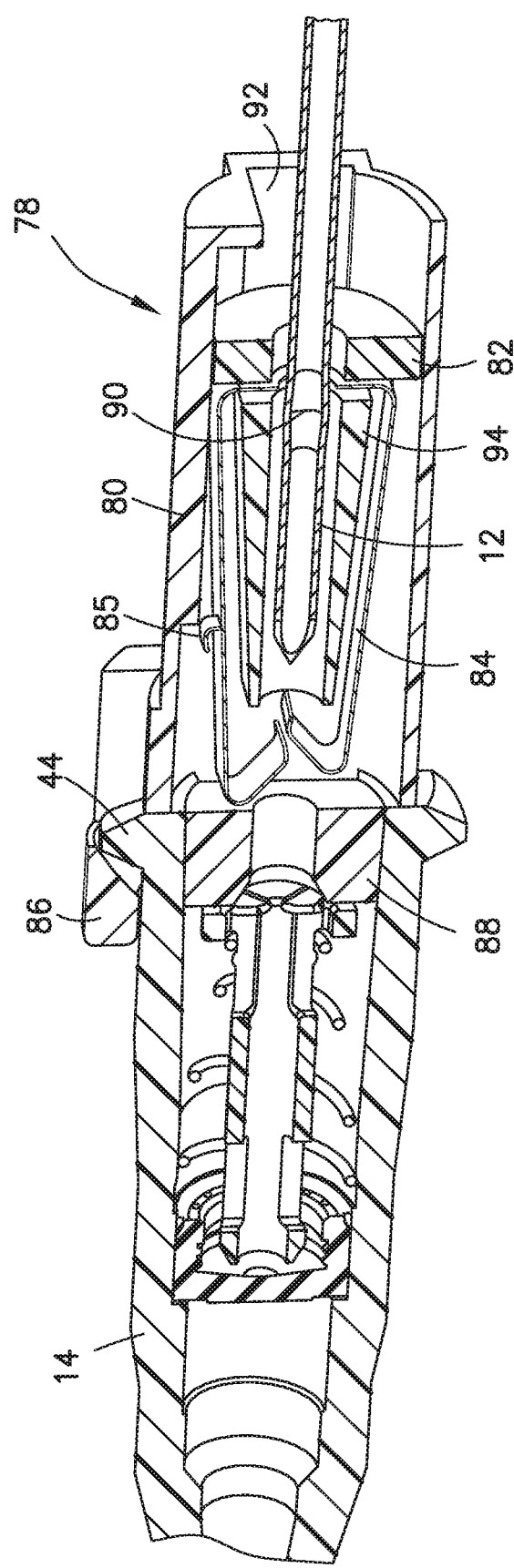
FIG. 14 is a sectional, side view of the exemplary needle shield of FIG. 13 with the needle withdrawn into the needle shield.

As the needle 12 is pulled further, the shaft of the needle slides through the needle shield 78 until a deformation 90, for example a crimp or protrusion formed near the distal end of the needle 12 to increase its diameter, engages the clip base as shown in FIG. 14. The opening in the clip base is sized to allow passage of the needle shaft, but not the deformation 90. Thus, when the tip of the needle 12 is in the closed position of the clip 84, the deformation 90 is also enclosed by the clip 84.

Figure 15:
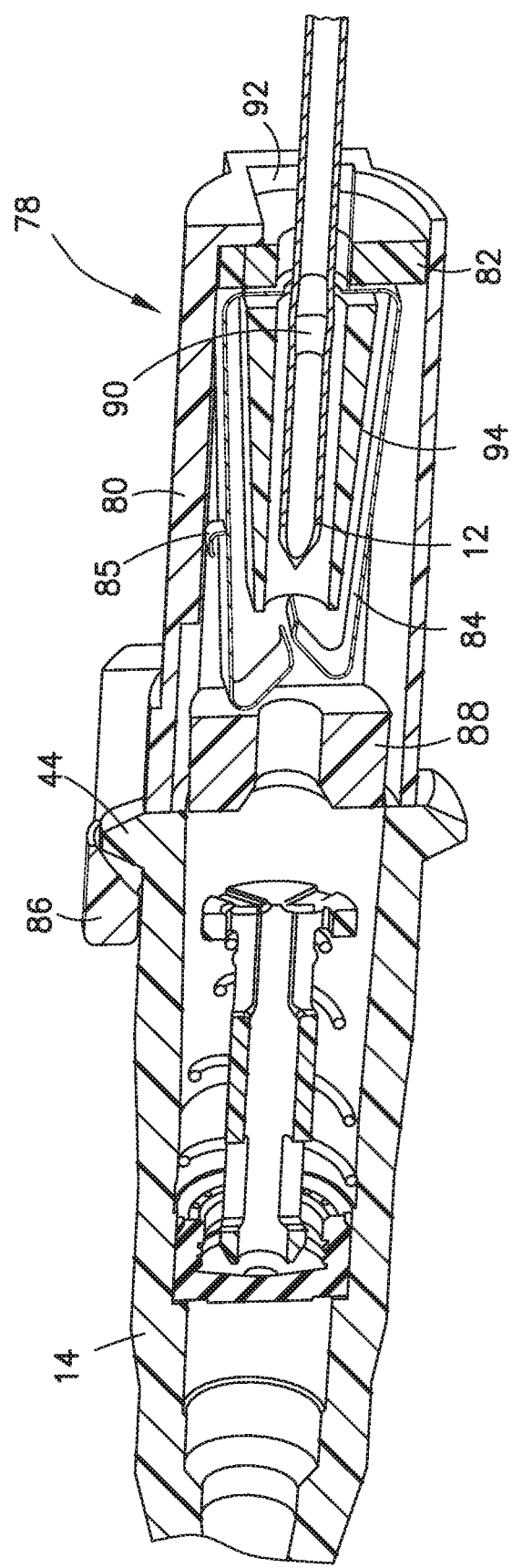
FIG. 15 is a sectional, side view of the exemplary needle shield of FIG. 13 with the inner sleeve withdrawn from the catheter hub and into the outer sleeve.
Figure 16:
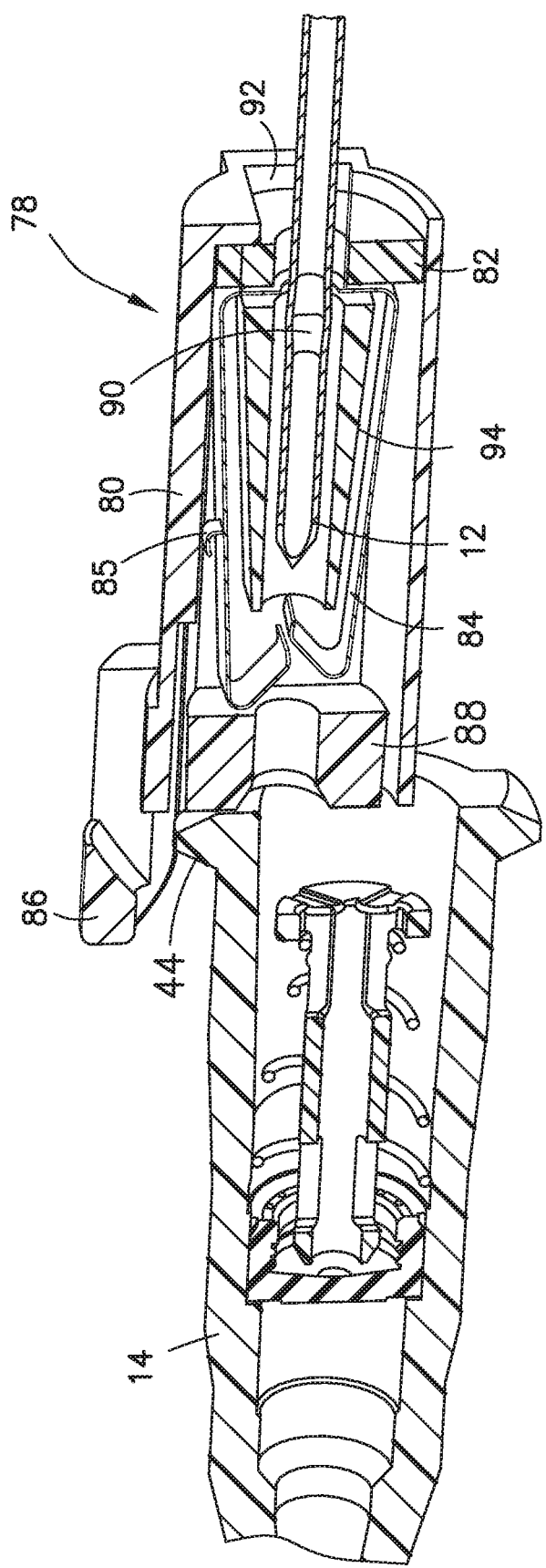
FIG. 16 is a sectional, side view of the exemplary needle shield of FIG. 13 with the needle shield being removed from the catheter hub.

Further movement of the needle 12 including the deformation 90 results in the inner sleeve 82 being drawn further into the outer sleeve 80, removing the opposing member 88 from the catheter hub 14 as shown in FIG. 15. Specifically, the inner sleeve 82 moves relative to the outer sleeve 80. When the opposing member 88 is withdrawn from the catheter hub 14, the needle shield 78 can be moved radially relative to the catheter hub 14. The catch 86 can then be lifted from the Luer thread protrusion 44 and the needle shield 78, needle 12, and needle hub 16 can be separated from the catheter hub 14.

In the exemplary embodiment shown in FIGS. 11 and 12, after the needle shield 20 is removed, distal movement of the inner sleeve 28 relative to the outer sleeve 26 in the axial direction can cause the foot 54 to engage the slot 40, resisting separation of the inner sleeve 28 and the outer sleeve 26 and possible exposure of the needle 12 tip. The engagement of the needle deformation 90 and the clip base 60 prevents the needle 12 from being withdrawn from the needle shield 20 in the proximal direction. The features of the exemplary embodiments of FIGS. 11 and 12 may be combined with features of the other exemplary embodiments disclosed herein as appropriate.

The needle shield 78 depicted in FIGS. 13-16 is similar to the needle shield 20 depicted in FIGS. 3-12. The outer sleeve 80 of the needle shield in FIGS. 13-16 includes one or more keyway grooves 92 extending from a rounded surface. The keyway grooves 92 prevent rotation of the inner sleeve 82 relative to the outer sleeve 80. The inner sleeve 82 includes a frusto-conical clip retainer 94 tapering from the proximal end to the distal end. The sides of the clip retainer 94 are configured to abut the clip 84 when it is in the closed orientation.

In various exemplary embodiments, the clip retainer 94 has a surface that extends so that one of the hooks rests on the clip retainer 94 (not shown) throughout the removal of the needle 12. In this configuration, only a single arm moves from the open orientation to the closed orientation. The use of a single moving arm reduces friction on the needle 12 and helps prevent binding during the needle's withdrawal from the catheter hub 14. In certain embodiments, the needle shield is configured to use a clip with only a single arm, although two arms are beneficial in certain applications to balance the clip and resist tilting of the clip's base relative to the needle 12. The features of the exemplary embodiments of FIGS. 13-16 may be combined with features of the other exemplary embodiments disclosed herein as appropriate.

Figure 17A:
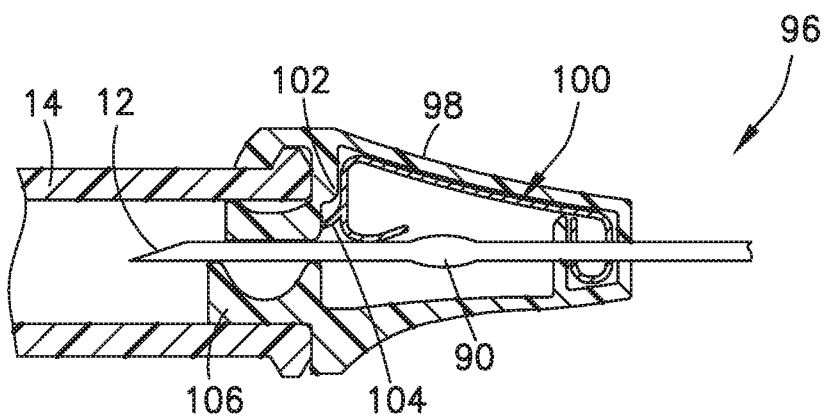
FIGS. 17A-C illustrates another exemplary embodiment of a needle shield being connected, and then removed from, a catheter hub.
Figure 17B:
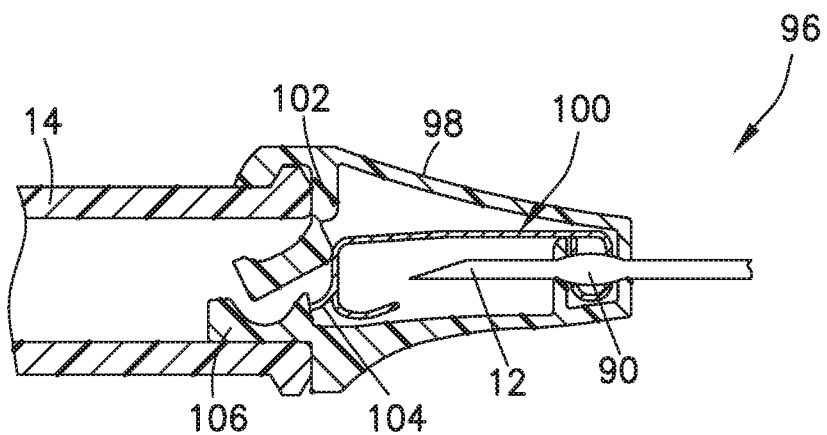
Figure 17C:
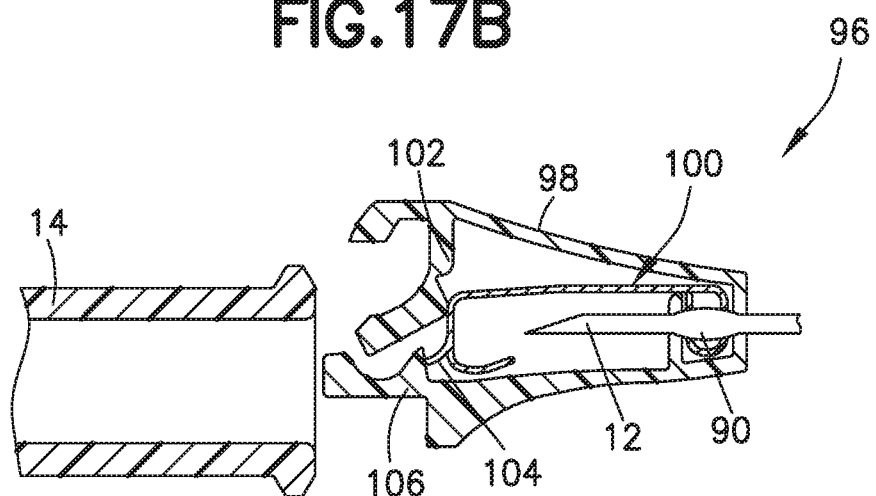

FIGS. 17A-17C depict another exemplary embodiment of the needle shield 96 having an outer sleeve 98 and a metal clip 100 with a single arm, omitting the inner sleeve. The outer sleeve 98 has latch 102 acting as an opposing member. The latch 102 has a first arm extending from an inner surface of the outer sleeve 98 and a second arm hinged to the first arm, for example by a living hinge. The clip 100 includes a hook having a tab 104 extending in the distal direction to abut the latch 102. The tab 104 and/or the inserted needle 12 may retain the latch 102 in the closed configuration, prevent radial movement of the needle shield 96 with respect to the catheter hub 14 and therefore resist disengagement of the catch from the Luer thread.

As the needle 12 is withdrawn into the needle shield 96, the clip 100 moves into a closed position, disengaging the tab 104 from the latch 102 and allowing the latch 102 to open as shown in FIG. 17B. After the latch 102 is opened, the needle shield 96 can be disengaged from the catheter hub 14, as shown in FIG. 17C. In the closed position, the tab 104 may or may not engage a bottom protrusion 106, preventing the needle 12 and metal clip 100 from exiting the needle shield 96 in the distal direction. The engagement of the needle deformation 90 and the clip base prevents the needle 12 from being withdrawn from the needle shield 96 in the proximal direction. The features of the exemplary embodiments of FIGS. 17A-17C may be combined with features of the other exemplary embodiments disclosed herein as appropriate.

Figure 18:
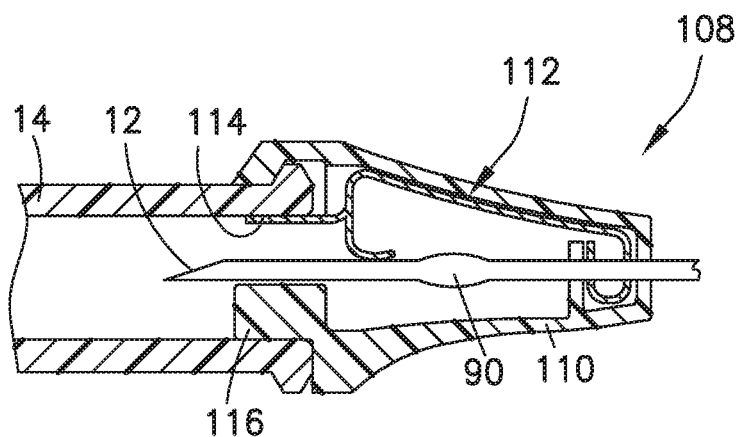
FIG. 18 illustrates another exemplary embodiment of a needle shield connected to a catheter hub.

FIG. 18 depicts another exemplary embodiment of the needle shield 108 having an outer sleeve 110 and a metal clip 112 with a single arm, omitting the inner sleeve. The clip 112 includes a hook having a tab 114 extending in the distal direction to act as the opposing member. The tab 114 engages an inner surface of the catheter hub 14 to resist radial movement of the needle shield 108 with respect to the catheter hub 14. As the needle 12 is withdrawn into the needle shield 108, the arm moves into a closed position, disengaging the tab 114 from the catheter hub. This allows the needle shield 108 to disengage the catheter hub 14. In the closed position, the hook engages a bottom protrusion 116, preventing the needle 12 and clip 112 from exiting the needle shield 108 in the distal direction. The engagement of the needle deformation 90 and the clip base prevents the needle 12 from being withdrawn from the needle shield 108 in the proximal direction. The features of the exemplary embodiments of FIG. 18 may be combined with features of the other exemplary embodiments disclosed herein as appropriate.

Figure 19:
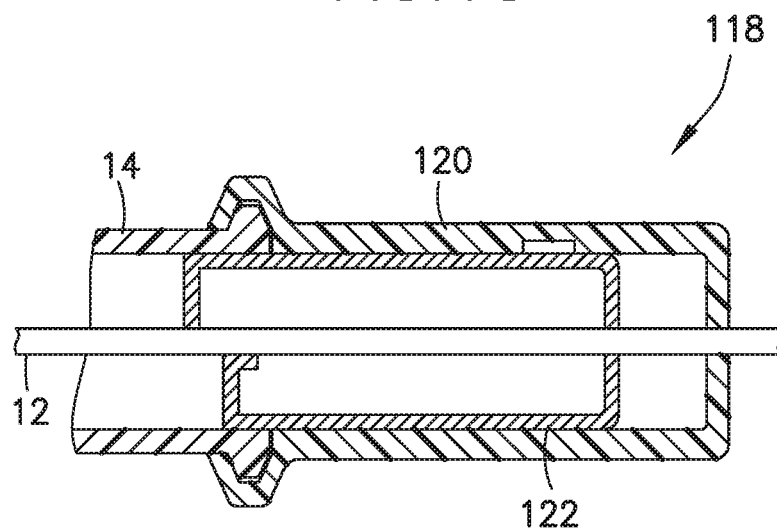
FIG. 19 illustrates another exemplary embodiment of a needle shield connected to a catheter hub.
Figure 20:
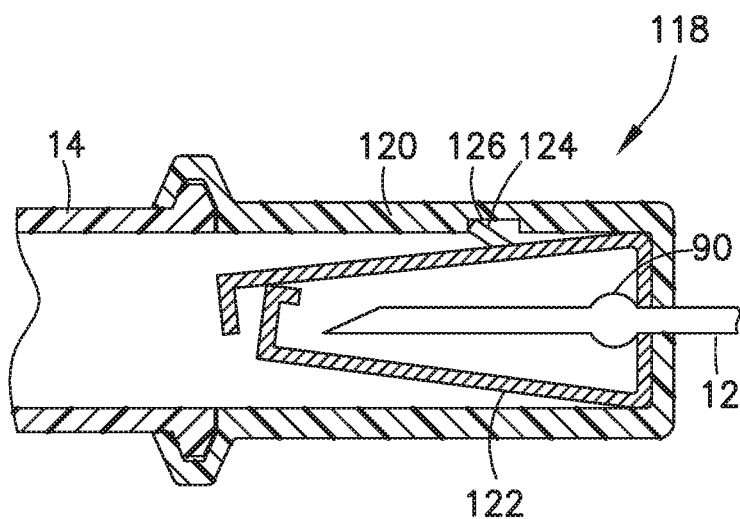
FIG. 20 illustrates another exemplary embodiment of a needle shield removed from a catheter hub.

FIGS. 19 and 20 depict another exemplary embodiment of the needle shield 118 having an outer sleeve 120 and a metal clip 122 with a first and second arm, omitting the inner sleeve. The first and second arms extend into the catheter hub 14 to engage an inner surface of the catheter hub 14 and act as the opposing member. As the needle 12 is withdrawn into the needle shield, the arms move into a closed position. In certain embodiments, the closed position provides enough clearance for the needle shield 118 to be removed from the catheter hub 14. In alternative embodiments, the needle 12 engaging the clip 122 moves the clip 122 inside of the outer sleeve 120 so that the first and second arms are completely withdrawn from the catheter hub 14 before the needle shield 118 can be disengaged.

As shown in FIG. 20, a tab 124 may extend from one of the arms. The tab 124 is angled so that it can be moved proximally into a slot 126 formed in the outer sleeve 120. The angle of the tab 124 engages a side of the slot 126 to resist distal movement of the clip 122 and needle 12 after the needle shield 118 has been removed from the catheter hub 14. Engagement of the needle deformation 90 with the clip 122 prevents the needle 12 from being removed from the needle shield 118 in the proximal direction. The features of the exemplary embodiments of FIGS. 19 and 20 may be combined with features of the other exemplary embodiments disclosed herein as appropriate.

Figure 21A:
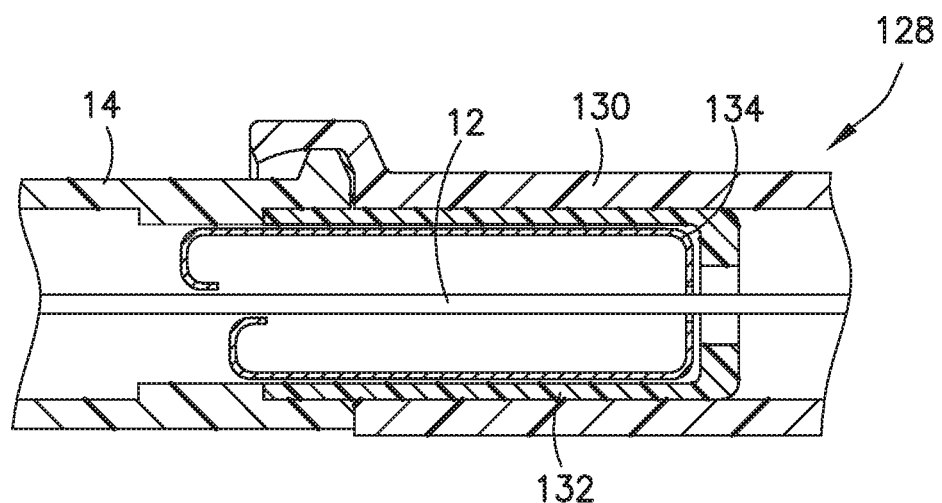
FIG. 21A illustrates another exemplary embodiment of a needle shield connected to a catheter hub.
Figure 21B:
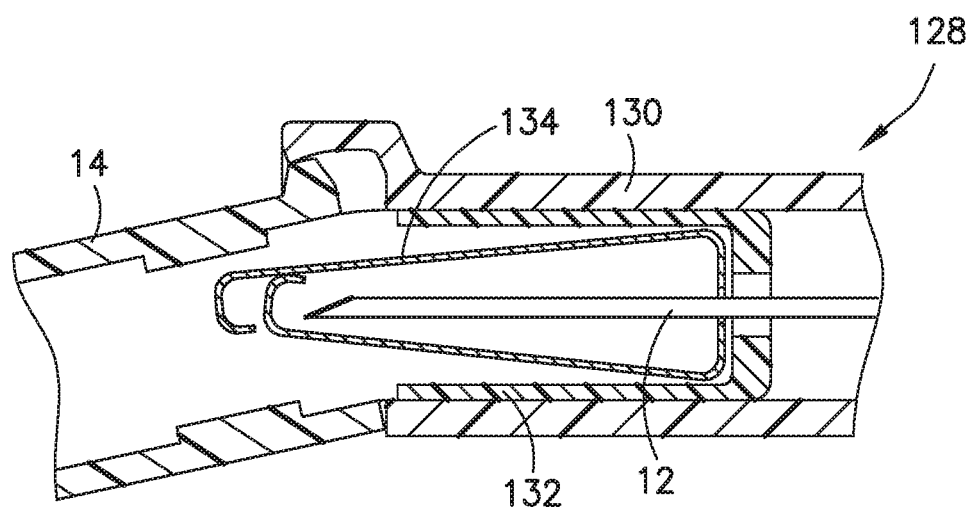
FIG. 21B is an enlarged view of FIG. 21A showing the engagement of the outer sleeve and inner sleeve with the catheter hub.

FIGS. 21A and 21B depict another exemplary embodiment of the needle shield 128 having an outer sleeve 130, an inner sleeve 132, and a clip 134 with a first and second arm.

The inner sleeve 132 extends into and abuts an inner surface of the catheter hub 14, acting as the opposing member. As the needle 12 is withdrawn into the needle shield 128, the arms move into a closed position and the clip 134 pulls the inner sleeve 132 out of the catheter hub 14 and into the outer sleeve 130. Disengagement of the inner sleeve 132 from the catheter hub 14 allows the needle shield 128 to be disengaged from the catheter hub 14. The features of the exemplary embodiments of FIGS. 21A and 21B may be combined with features of the other exemplary embodiments disclosed herein as appropriate.

Figure 22A:
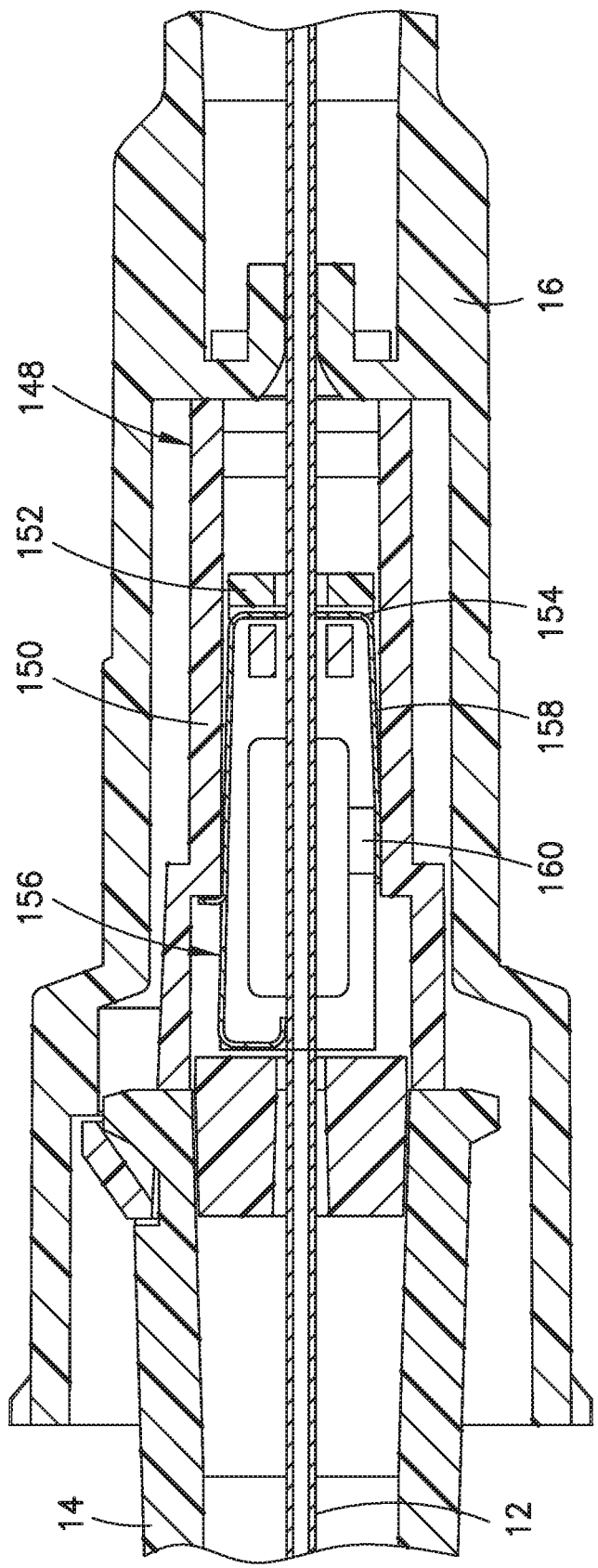
FIG. 22A is a sectional, side view of another exemplary embodiment of a needle shield connected to a catheter hub.
Figure 24A:
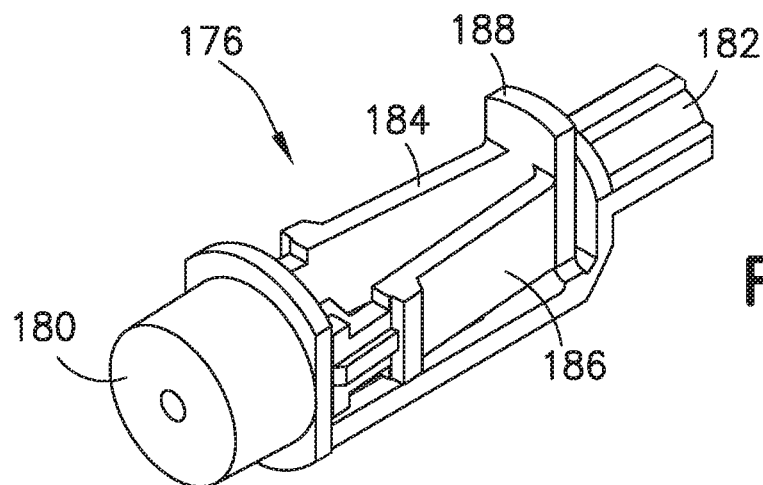
FIGS. 24A-D are perspective views of an exemplary inner sleeve with an integral clip.
Figure 24B:
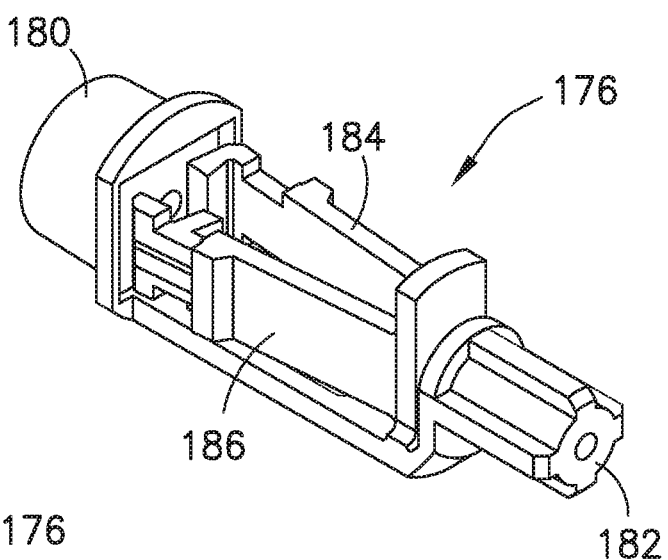
Figure 24C:
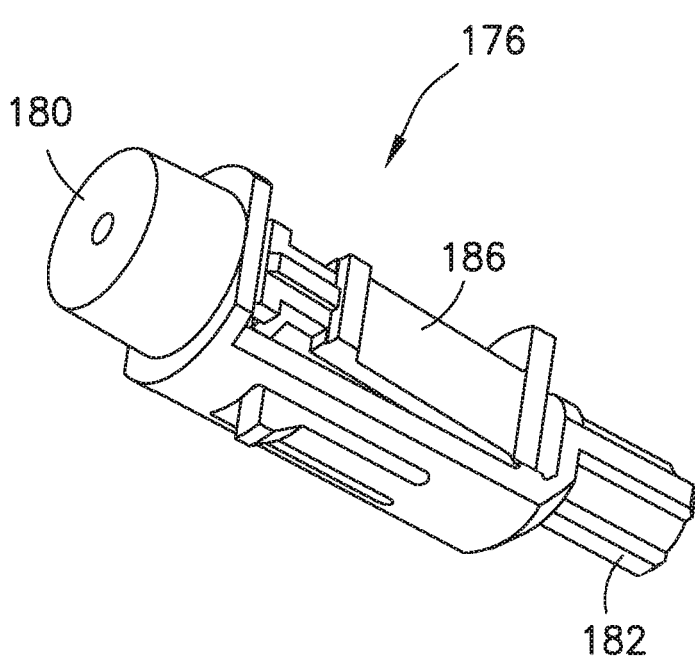
Figure 24D:
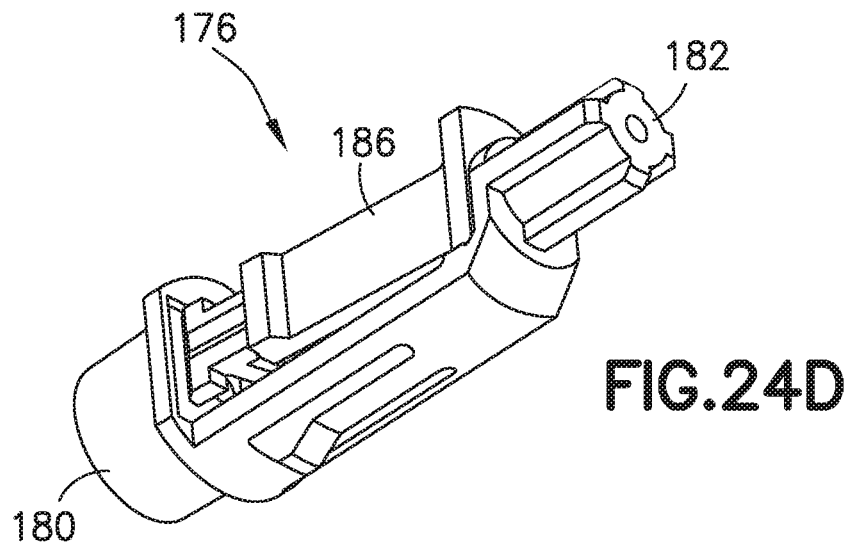
Figure 24E:
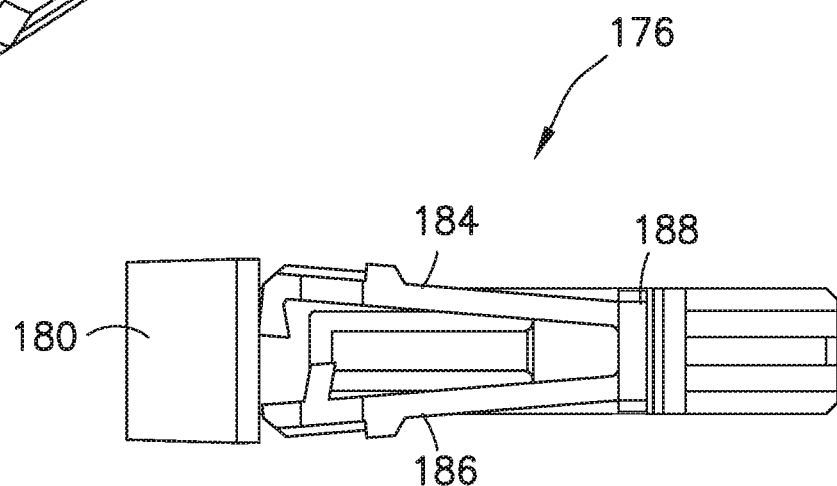
FIG. 24E is a top view of the inner sleeve with an integral clip shown in FIG. 24A.
Figure 24F:
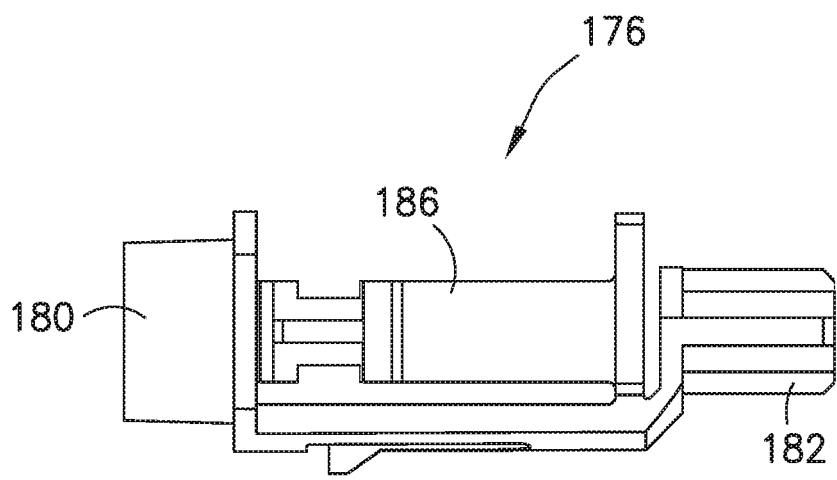
FIG. 24F is a right side view of the inner sleeve with an integral clip shown in FIG. 24A.
Figure 24G:
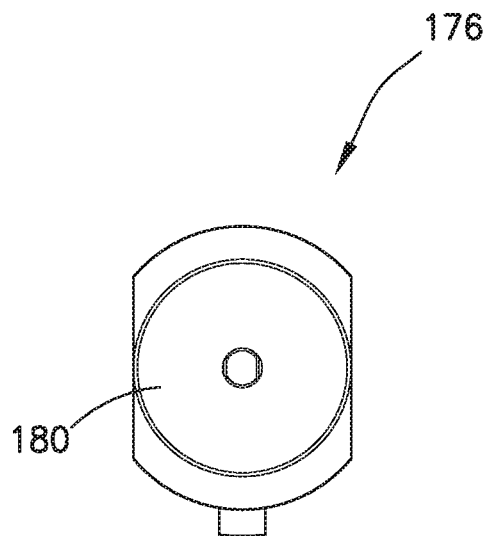
FIG. 24G is a front view of the inner sleeve with an integral clip shown in FIG. 24A.
Figure 24H:
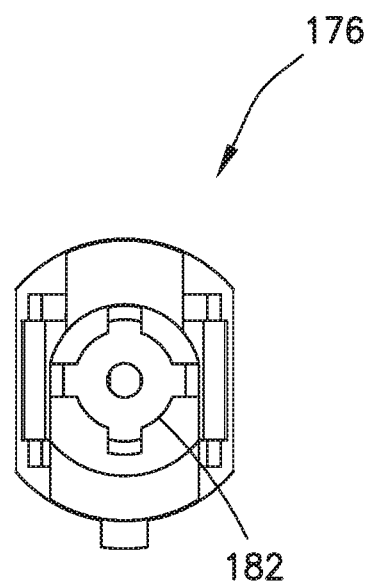
FIG. 24H is a rear view of the inner sleeve with an integral clip shown in FIG. 24A.
Figure 24I:
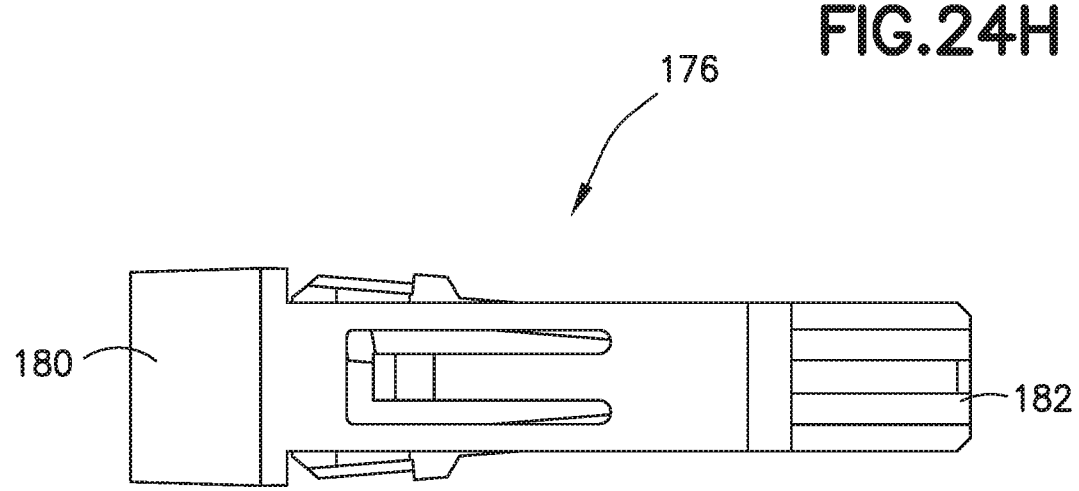
FIG. 24I is a bottom view of the inner sleeve with an integral clip shown in FIG. 24A.
Figure 26A:
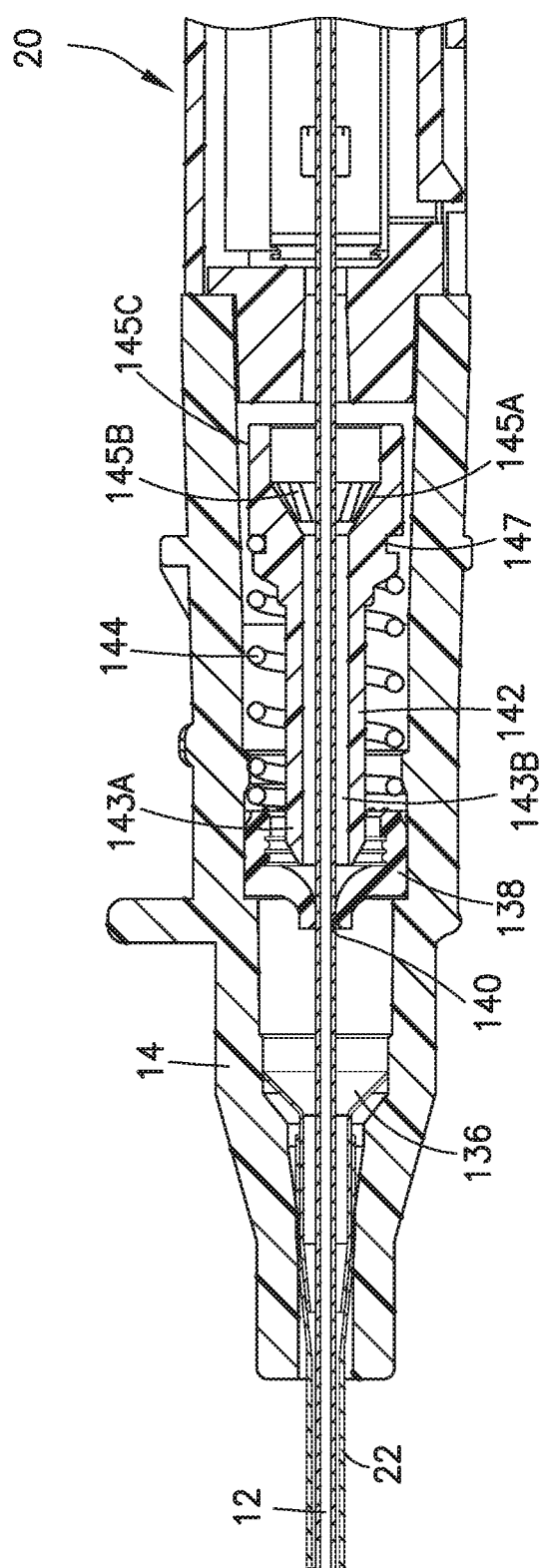
FIG. 26A is a sectional, side view of the catheter of FIG. 25A.
Figure 26D:
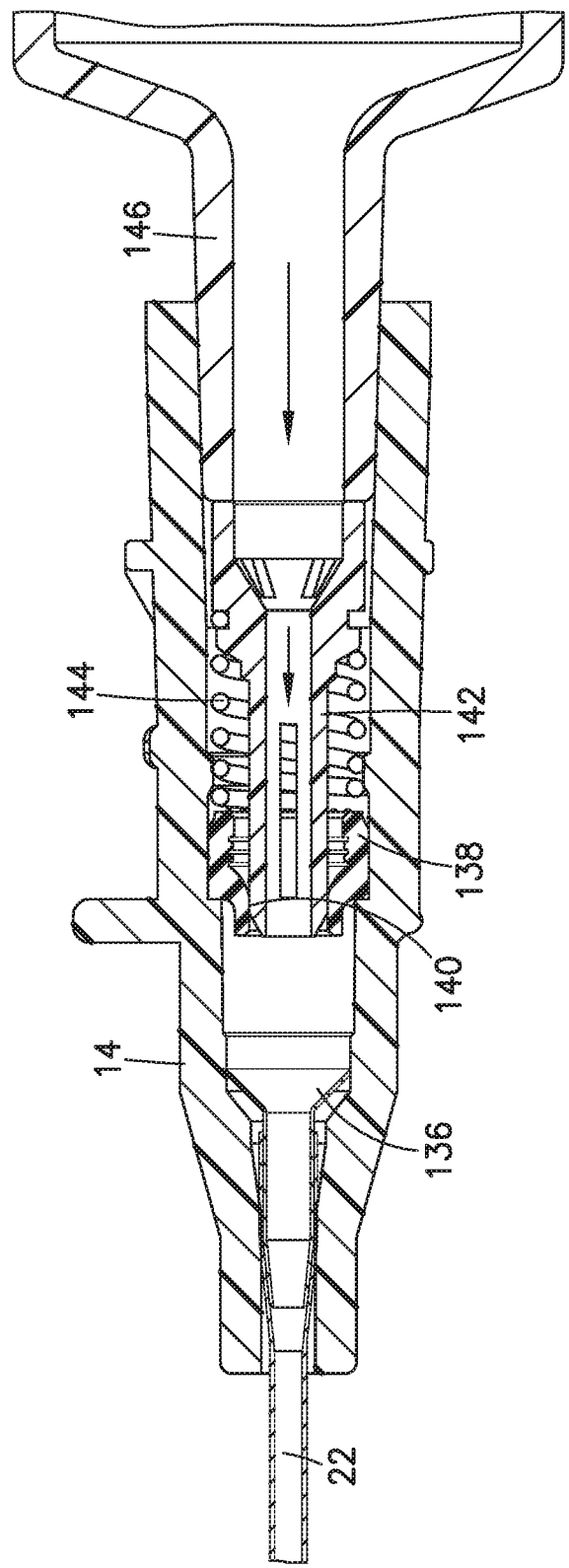
FIG. 26D is a sectional, side view of the catheter of FIG. 26C with the Luer connector pushing the actuator through the septum.
Figure 26E:
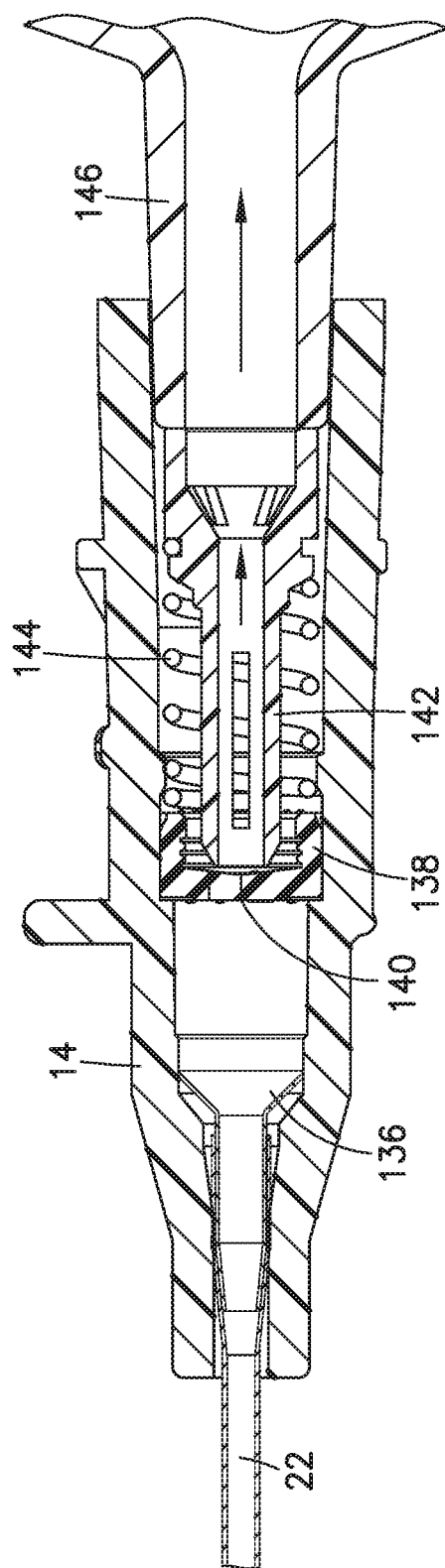
FIG. 26E is a sectional, side view of the catheter of FIG. 26D with the male Luer connector being withdrawn from the catheter hub.
Figure 26F:
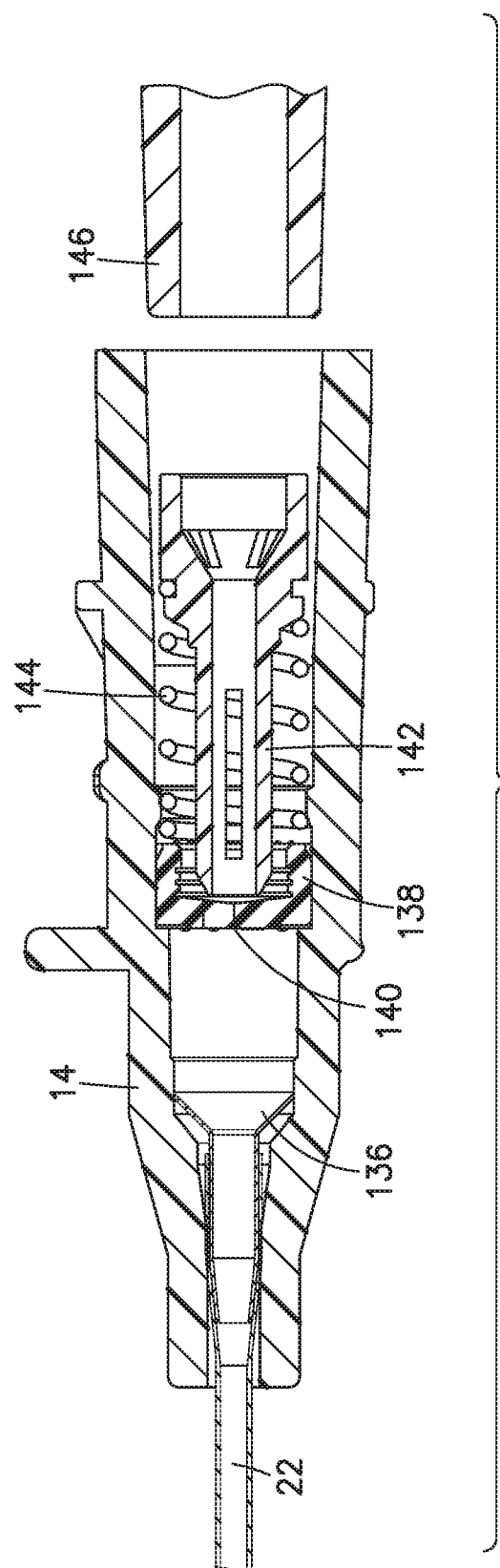
FIG. 26F is a sectional, side view of the catheter of FIG. 26E with the male Luer connector withdrawn from the catheter hub.

FIGS. 22A-22C depict another exemplary embodiment of the needle shield 148 having an outer sleeve 150, an inner sleeve 152, and a clip 154. The clip 154 has a first arm 156 and a second arm 158. The first arm 156 is moveable and includes a hook that captures the needle 12 when it is drawn into the inner sleeve 152 the appropriate amount. A protrusion 160 extends from the inner sleeve 152 to receive the second arm 158. The second arm 158 therefore does not engage the needle during its movement. In this configuration, only the first arm 156 moves from the open orientation to the closed orientation. The use of a single moving arm reduces friction on the needle 12 and helps prevent binding during the needle's withdrawal from the catheter hub 14. The features of the exemplary embodiments of FIGS. 22A-22C may be combined with features of the other exemplary embodiments disclosed herein as appropriate.

FIGS. 23A-23B depict another exemplary embodiment of the needle shield 162 having an outer sleeve 164, an inner sleeve 166, and a clip 168. The outer sleeve 164 includes a biasing member 170 that extends into and abuts the catheter hub 14. The biasing member 170 is a resilient material, for example a spring material or other elastomeric material that may be formed integrally with or connected to the outer sleeve 164. In various exemplary embodiments, the biasing member 170 may be formed as part of, or connected to, the clip 168. A housing 172 surrounds the needle shield 162. Initially, the opposing member of the inner sleeve 166, or clip 168, retains the biasing member 170 in a compressed state. When the inner sleeve 166 is drawn completely into the outer sleeve 164, the biasing member 170 biases the outer sleeve 164, assisting in moving the catch 174 away from the Luer thread. The features of the exemplary embodiments of FIGS. 23A and 23B may be combined with features of the other exemplary embodiments disclosed herein as appropriate.

FIGS. 24A-24I depict another exemplary embodiment of an inner sleeve 176 having an integral or unitary clip. The inner sleeve 176 and clip combination may be made from a single piece of metal or plastic, or they may be made from separate pieces of material that are integrally molded together. The inner sleeve 176 includes an opposing member 180 extending in a distal direction to enter the catheter hub (not shown) and an outer member 182 extending in a distal direction to enter the outer sleeve (not shown). The outer member 182 has a central cylindrical portion with one or more radially extending ribs. The clip portion of the inner sleeve 176 has a first arm 184 and a second arm 186 extending from a distal wall 188. The first and second arms 184, 186 are moveable between an open and closed orientation to receive and contain the tip of a needle (not shown). The features of the exemplary embodiments of FIGS. 24A-24I may be combined with features of the other exemplary embodiments disclosed herein as appropriate.

Any of the needle shields described above can be used in connection with a multi-use, Luer actuated blood control catheter hub as depicted in FIGS. 25A-26F. The catheter includes a catheter hub 14 and a flexible catheter tube extending from the catheter hub. A metal wedge 136 is positioned in the catheter hub to retain the catheter tube. A septum 138 is positioned to control fluid flow through the catheter hub 14. As best shown in FIG. 25B, the septum 138 has one or more resilient openings or slits 140 designed to selectively prevent unwanted fluid flow through the septum 138. The septum 138 has three slits 140 forming three triangular flaps that open when engaged by an actuator 142. The septum 138 is made from an elastic material, for example silicone rubber.

The septum 138 further includes a plurality of axial flow channels 139. The flow channels 139 are disposed on an outer circumference of the septum 138. Eight flow channels 139 equidistant from each other are illustrated, although various quantities and positions are contemplated. The flow channels 139 have an appropriate width and depth so that when the septum 138 is not pierced, blood can enter and air can escape the distal end of the septum 138 in the front portion of the catheter hub. At the same time, the flow channels 139 are sized small enough to prevent the blood from exiting past the septum 138 (at least for some period of time). Such a configuration is possible because the intermolecular forces in the blood are greater than the intermolecular forces in air. The septum 138 shown in FIG. 25B may be used in any of the embodiments discussed herein. Other septum configurations may be used as would be understood by one of ordinary skill in the art.

An actuator 142 and a biasing or return member, for example a metal or plastic compression spring 144, are positioned in the catheter hub 14. The actuator 142 engages the septum 138 to open the slits 140 and permit fluid flow through the catheter hub 14. The biasing or return member 144 is capable of returning the actuator 142 to a position that allows the resilient slits 140 to close, preventing fluid flow through the catheter hub 14.

The actuator 142 has an actuator barrel 143A surrounding an internal passage 143B. The actuator barrel 143A is a substantially tubular member and the internal passage 143B is substantially cylindrical. The tubular member has one or more openings 143C to permit fluid flow through and around the actuator barrel. A first end of the actuator barrel has a nose with a chamfered outer surface to engage the septum. A frusto-conical section 145A extends from the second end of the actuator barrel 143A. The frusto-conical section 145A has one or more openings 145B to permit fluid flow therethrough. A cylindrical section 145C extends from the frusto-conical section 145A to engage a male Luer connector. One or more hooks having an angled front surface and a slot 147 extend from the actuator barrel 143A.

In the exemplary embodiment shown in FIGS. 25A-26F, the biasing or return member is a spring 144, for example a helical compression spring with a distal end and a proximal end. The spring 144 may be made from metal, plastic, an elastomer, or another suitable resilient material. The distal end of the spring 144 forms an interference fit with the inner surface of the catheter hub 14. The interference fit may be sufficient to retain the spring 144, even during loading, or the distal end of the spring 144 may also abut the septum 138. The proximal end of the spring 144 connects to the actuator 142, for example by fitting over a hook and into the slot. In other embodiments 142, the actuator 142 and the biasing member 144 are combined to be a unitary structure. In various exemplary embodiments, the inner surface of the catheter hub 14 and/or the outer surface of the actuator 142 and/or biasing member 144 include undercuts, bumps, projections, tines, or other suitable structure to form a snap connection between the catheter hub 14 and between the biasing member 144, and the biasing member 144 and the actuator 142.

FIGS. 26A-26F depict the operation of the catheter hub 14 with the actuator 142 and biasing member 144. The introducer needle 12 initially extends through the actuator 142, the septum 138, the wedge 136, and the catheter tube 22. After the introducer needle 12 and the catheter tube 22 are inserted into a patient, the needle 12 is withdrawn, closing the septum 138. As the male Luer connector 146 is inserted into the catheter hub 14, the Luer connector 146 abuts and moves the actuator 142 in the distal direction, compressing the spring 144. Further insertion of the Luer connector 146 moves the actuator 142 through the septum 138, opening the slits 140 and allowing fluid to flow through the catheter hub 14.

When the Luer connector 146 is removed, the spring 144 removes the actuator 142 from the septum 138, closing the slits 140 and preventing fluid from flowing therethrough. This allows the catheter assembly to be reused through multiple Luer connections, as opposed to a single use catheter where the actuator 142 would remain in the septum 138 after a Luer connector is removed. However, a single-use catheter without the actuator 142 and/or spring 144 can also be used with the needle shields described herein. The features of the exemplary embodiments of FIGS. 25A-26F may be combined with features of the other exemplary embodiments disclosed herein as appropriate.

FIG. 27 illustrates an exemplary embodiment of an actuator 254. The actuator 254 can be used in any of the embodiments disclosed herein. The actuator 254 includes a nose 258 that reduces friction when the actuator 254 penetrates into a septum 238 of a catheter hub assembly. The actuator 254 further includes openings 255 that extend through the actuator 254 in a direction perpendicular to a centerline of the actuator 254. For example, the actuator 254 can include two rectangular shaped openings 255, although more or less are contemplated.

The actuator 254 also includes a plurality of grooves 257 that extend axially along the distal portion of an outer surface of the actuator 254 in a plane parallel to the centerline of the actuator 254. For example, four grooves 257, substantially radially equidistant from each other, can be present along an external surface of the distal portion of the actuator 254, although more or less grooves 257 are contemplated. The grooves 257 can be of varying depths into the actuator 254. The grooves 257 are different from the openings 255 because the grooves 257 do not extend completely through the thickness of the actuator 254.

The openings 255 and the grooves 257 advantageously provide increased area for the fluid to move inside the catheter hub assembly. The increased area advantageously allows for fluid flushing and to prevent coagulation of fluid in the proximal and distal ends of the septum. Additionally, the openings 255 and the plurality of grooves 257 advantageously minimize the stagnation of fluid and allow for greater mixing. The grooves 257 further prevent the septum from sealing on an outside surface of the actuator in operation. By not forming a sealing interface, the fluid is permitted to leak through the septum via the grooves 57 and provide additional flushing.

Figure 28A:
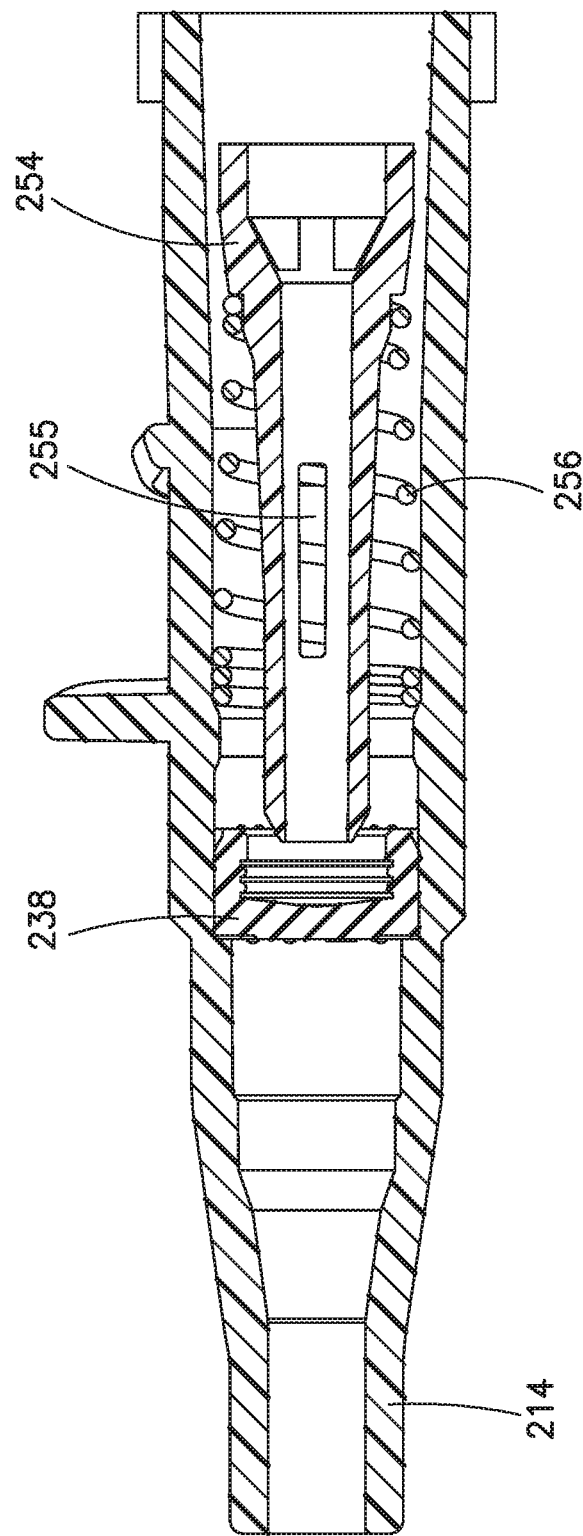
FIG. 28A illustrates a cross sectional view of the actuator of FIG. 27 in a catheter hub assembly.

FIG. 28A illustrates the actuator 254 of FIG. 27 in the catheter hub assembly. Similar to the embodiments described above, the catheter hub assembly further includes a catheter hub 214, a septum 238 and a biasing member 256. As illustrated, the openings 255 and the grooves 257 of the actuator 254 provide more area for fluid flow inside the catheter hub 214, thus achieving the advantages described above.

Figure 28C:
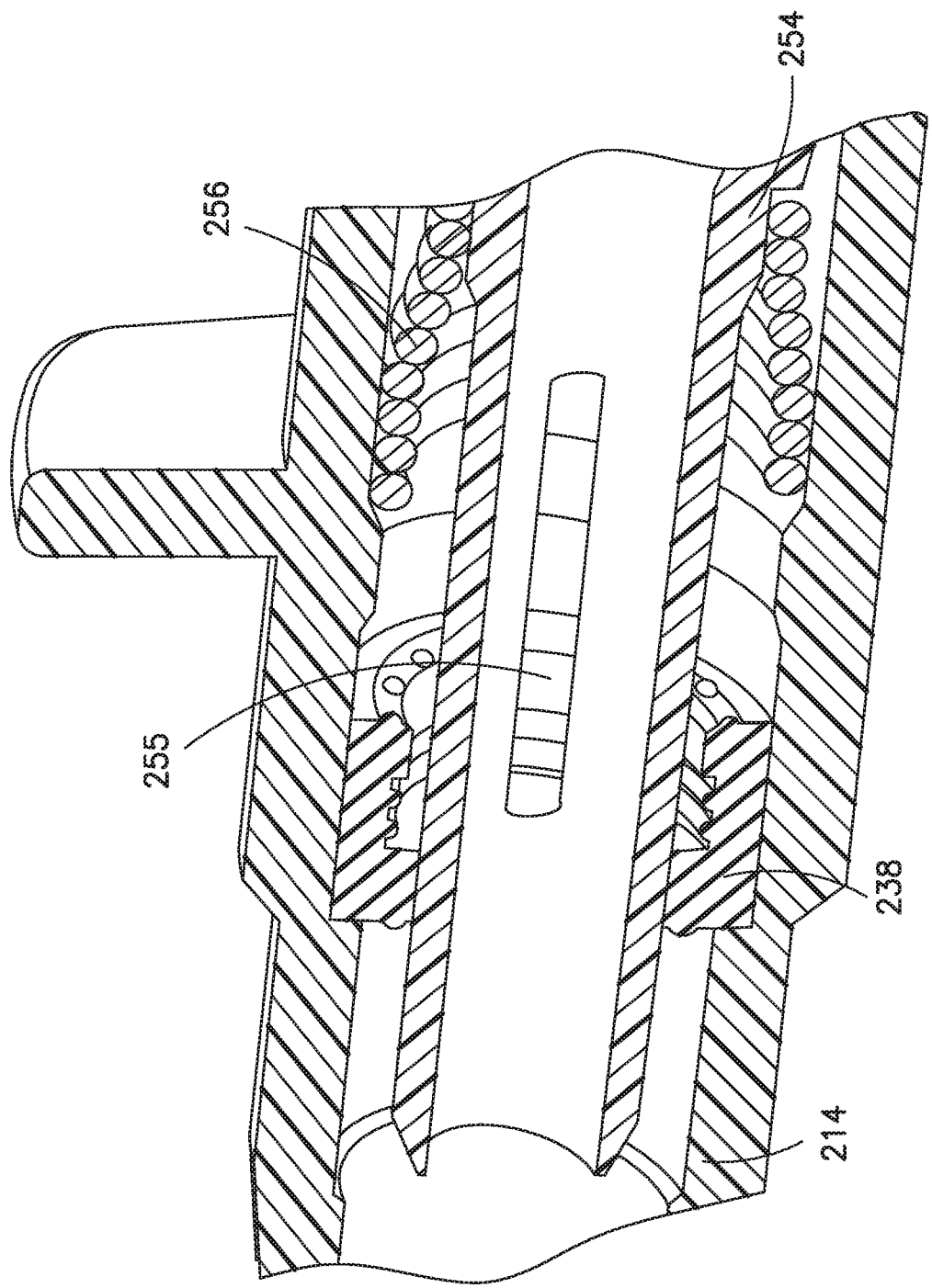
FIG. 28C illustrates a left perspective cross sectional view of the catheter hub assembly of FIG. 28A when piercing a septum.

FIGS. 28B and 28C illustrate the catheter hub assembly when the biasing member 256 is compressed and the actuator 254 pierces the septum 238. The catheter hub assembly may be configured such that the openings 255 and/or the grooves 257 of the actuator 254 optionally pierce or penetrate the septum 238. In the embodiment shown, the openings 255 in the actuator 254 do not penetrate the septum 238. However, the grooves 257 in the actuator 254 penetrate the septum 238. This configuration allows for increased fluid flow from the proximal end to the distal end of the septum 38 through the grooves 257, in addition to the advantages described above. After operation of the catheter assembly is complete, the actuator 254 is retracted from the septum 238 via the force exerted by the biasing member 256. The catheter assembly is configured for multiple uses upon depression of the actuator 254. The features described in this embodiment, such as the actuator, can be used in combination with the features described throughout this application.

Figure 29A:
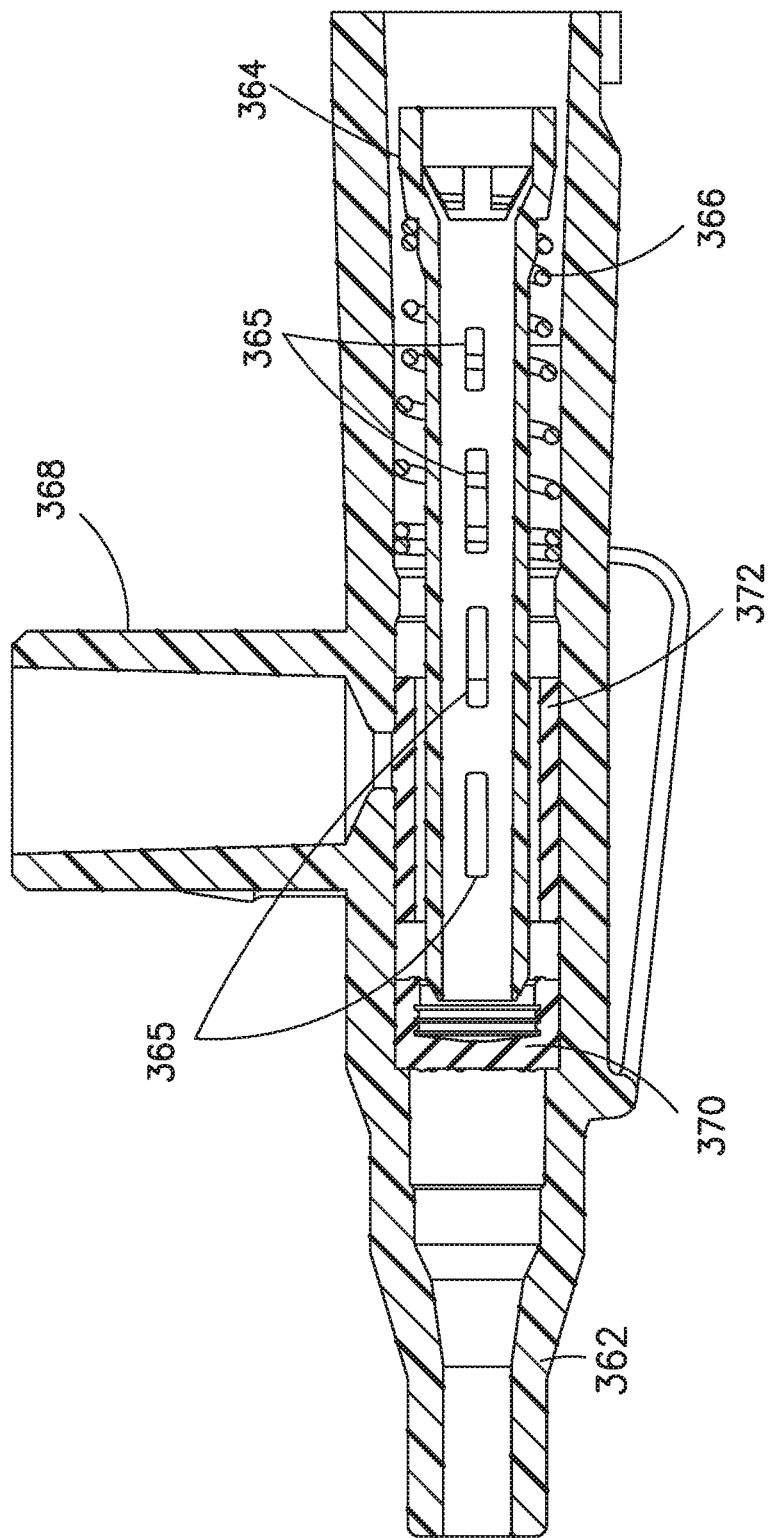
FIG. 29A illustrates a cross sectional view of another exemplary embodiment of a catheter hub assembly.

FIG. 29A illustrates another embodiment of an actuator 364 in a catheter hub assembly. The catheter hub assembly includes a catheter hub 362 having a side port 368. The side port 368 provides secondary access to the fluid flow in the catheter hub 362. The intersection of the main bore of the catheter hub 362 and the side port 368 includes a sleeve 372. The sleeve 372 provides selective fluid communication between the side port 368 and the catheter hub 362. Specifically, when sufficient fluid pressure is applied through the side port 368, the sleeve 372 compresses. The compression of the sleeve 372 allows for fluid to enter the catheter hub 362. Reference is made to U.S. Pat. No. 4,231,367, incorporated by reference herein, for a side port catheter in a catheter assembly of the type described herein. The catheter hub assembly further includes a septum 370 and a biasing member 366 that provides tension to the actuator 364.

The actuator 364 includes a plurality of openings 365 that extend through the actuator 364 in a similar manner as described above. The actuator 364 includes two rows of four openings 365 having different sizes and spacing, although various quantities, sizes and spacing of the openings 365 are contemplated. As illustrated, the openings 365 provide more area for fluid flow inside the catheter hub 362, thus achieving similar advantages described above with respect to FIGS. 27-28C.

Figure 29B:
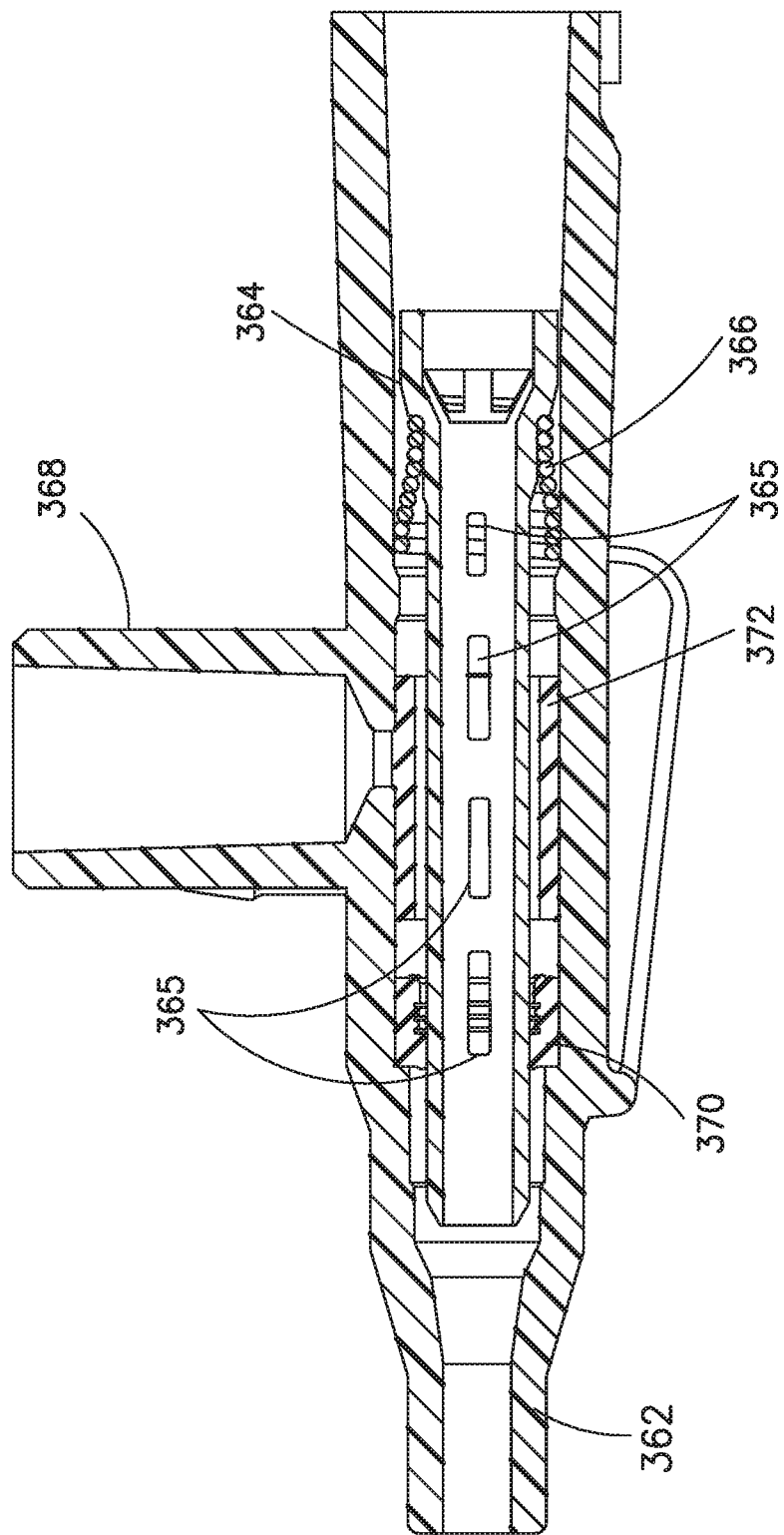
FIG. 29B illustrates the cross sectional view of the catheter hub assembly of FIG. 29A when piercing a septum.

FIGS. 29B and 29C illustrate the catheter hub assembly when the actuator 364 pierces the septum 370 and compresses the biasing member 366. The catheter hub assembly is configured such that the openings 365 of the actuator 364 optionally pierce the septum 370. In the embodiment shown, the openings 365 in the actuator 364 do not pierce the septum 370. This configuration allows for increased fluid flow between the side port 368 and the catheter hub 362 at the proximal end of the septum 370, in addition to the advantages described above. If the openings 365 in the actuator 364 pierce the septum 370, increased mixing of fluid would also take place at a distal end of the septum 370.

When operation of the catheter assembly is complete, the actuator 364 is retracted from the septum 370 via the force exerted by the biasing member 366. The catheter assembly is configured for multiple uses upon depression of the actuator 364. The features described in this embodiment, including the actuator, can be used in combination with the features described throughout this application.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

What is claimed is:

1. A catheter assembly comprising: a flexible catheter; a catheter hub; a needle having a distal tip, the needle disposed in the flexible catheter and moving from a first position that exposes the needle to a second position; an outer member that is configured to directly engage and disengage the catheter hub; an inner member engaged to and movably disposed in the outer member; and a needle protection member that encloses at least a portion of the needle when the needle is in the second position; wherein when the needle is moved to the second position, the inner member axially moves relative to the outer member to allow the outer member to disengage from the catheter hub.

2. The catheter assembly according to claim 1, wherein when the needle is in the first position, the inner member engages the catheter hub.

3. The catheter assembly according to claim 1, wherein the outer member includes a slot that extends through a bottom wall of the outer member.

4. The catheter assembly according to claim 3, wherein the inner member includes an elastic leg on a bottom surface of the inner member, a distal end of the elastic leg includes a protrusion that is configured to engage the slot of the outer member.

5. The catheter assembly according to claim 4, wherein the protrusion of the inner member is engaged to the slot of the outer member when the needle is in the first and second positions.

6. The catheter assembly according to claim 4, wherein the protrusion of the inner member is disposed at a distal end of the slot of the outer member when the needle is in the first position.

7. The catheter assembly according to claim 4, wherein the protrusion of the inner member is disposed at a proximal end of the slot of the outer member when the needle is moved toward the second position.

8. The catheter assembly according to claim 4, wherein the elastic leg of the inner member is a cantilever arm.

9. The catheter assembly according to claim 3, wherein the slot is adjacent to a distal end of the outer member.

10. The catheter assembly according to claim 1, wherein the inner member deforms in the outer member to provide retention.

11. The catheter assembly according to claim 10, wherein the inner member axially moves in the outer member during operation and upon applying a predetermined force.

12. The catheter assembly according to claim 1, wherein the inner member includes a slot that extends through a bottom wall of the inner member; and
the outer member includes an elastic leg, a distal end of the elastic leg includes a protrusion that is configured to engage the slot of the inner member.

13. The catheter assembly according to claim 1, wherein the needle protection member comprises a resilient clip, the resilient clip is disposed in the inner member.

14. The catheter assembly according to claim 1, wherein the needle protection member comprises an integrally formed resilient clip.

15. The catheter assembly according to claim 1, wherein the inner member includes one of a slot and an elastic leg;
the outer member includes an other of the slot and the elastic leg; and
a distal end of the elastic leg includes a protrusion that is configured to engage the slot.

16. A catheter assembly comprising:
a flexible catheter;
a catheter hub;
a needle having a distal tip, the needle disposed in the flexible catheter and moving from a first position that exposes the needle to a second position;
a housing that is configured to engage and disengage the catheter hub; and
a needle protection member disposed in the housing, the needle protection member enclosing at least a portion of the needle when the needle is in the second position; wherein
the housing engages the catheter hub when the needle is in the first position; and
when the needle is moved to the second position, the housing disengages catheter hub; wherein
the housing includes a rotating latch that is configured to engage an inner surface of the catheter hub.

17. The catheter assembly according to claim 16, wherein when the needle is in the first position, the housing engages an inner surface and an outer surface of the catheter hub.

18. The catheter assembly according to claim 16, wherein when the needle is in the first position, the needle protection member engages the rotating latch causing the rotating latch to engage the catheter hub.

19. The catheter assembly according to claim 16, wherein when the needle is in the second position, the needle protection member covers the distal tip of the needle, and the needle protection member disengages the rotating latch causing the rotating latch to disengage the catheter hub.

* * * * *